US 6,482,171 B1

(12) United States Patent
Corvi et al.

(10) Patent No.: US 6,482,171 B1
(45) Date of Patent: *Nov. 19, 2002

(54) MULTI-LUMEN CATHETER

(75) Inventors: Timothy J. Corvi, Belmont; John H. Stevens, Palo Alto, both of CA (US)

(73) Assignee: Heartport, Inc., Redwood City, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/782,113

(22) Filed: Jan. 13, 1997

Related U.S. Application Data

(63) Continuation-in-part of application No. 08/664,716, filed on Jun. 17, 1996, now Pat. No. 5,879,499, which is a continuation-in-part of application No. 08/612,230, filed on Mar. 7, 1996, now abandoned, which is a continuation-in-part of application No. 08/486,216, filed on Jun. 7, 1995, now Pat. No. 5,766,151, which is a continuation-in-part of application No. 08/282,192, filed on Jul. 28, 1994, now Pat. No. 5,584,803, which is a continuation-in-part of application No. 08/162,742, filed on Dec. 3, 1993, now abandoned, which is a continuation-in-part of application No. 08/123,411, filed on Sep. 17, 1993, now abandoned, which is a continuation-in-part of application No. 07/991,188, filed on Dec. 15, 1992, now abandoned, which is a continuation-in-part of application No. 07/730,559, filed on Jul. 16, 1991, now Pat. No. 5,370,685.

(51) Int. Cl.⁷ .............................................. A61M 29/00

(52) U.S. Cl. .................................... 604/96.01; 156/175

(58) Field of Search ................................ 604/282, 264, 604/280, 96, 925, 526, 527, 530–532, 96.01, 97.01; 156/166, 172, 176, 175, 293, 294

(56) References Cited

U.S. PATENT DOCUMENTS

| 150,960 A | 5/1874 | Isbell |
| 231,601 A | 8/1880 | Meigs |
| 243,396 A | 6/1881 | Pfarre |
| 280,225 A | 6/1883 | Noe |
| 299,622 A | 6/1884 | Chase |
| 303,757 A | 8/1884 | Sears et al. |
| 1,282,881 A | 10/1918 | Landis |

(List continued on next page.)

FOREIGN PATENT DOCUMENTS

| DE | 2246526 | 3/1973 |
| EP | 0 103 546 | 3/1984 |
| EP | 0 335 205 | 1/1985 |
| EP | 0 161 045 | 11/1985 |
| EP | 0 218275 | 4/1987 |
| EP | 0 249 338 | 5/1987 |

(List continued on next page.)

OTHER PUBLICATIONS

Andersen et al., "Transluminal Implantation of Artificial Heart Valves..." *European Heart Journal*, 1992;13:704–708.

Baxter Healthcare Corporation, "Fogarty Occlusion Catheter: Instructions for Use,"© 1994.

Buckberg, G.D., "Strategies and Logic of Cardioplegic Delivery to Prevent, Avoid, and Reverse Ischemic and Reperfusion Damage," *J Thorac Vasc Surg*, 1987; 93:127–129.

(List continued on next page.)

Primary Examiner—Sharon Kennedy

(57) ABSTRACT

A multi-lumen catheter having a reinforcing member wrapped around at least one of the lumens in a helical manner. An inflation lumen is positioned outside the reinforcing member for inflating a balloon carried by the catheter. A two-lumen extrusion is bonded to the reinforced lumen to form the multi-lumen catheter. The multi-lumen catheter is particularly useful as an aortic occlusion catheter.

2 Claims, 13 Drawing Sheets

U.S. PATENT DOCUMENTS

| | | |
|---|---|---|
| 2,029,236 A | 1/1936 | Klophaus |
| 2,308,484 A | 1/1943 | Auzin et al. |
| 2,531,730 A | 11/1950 | Henderson |
| 2,854,982 A | 10/1958 | Pagano |
| 3,326,648 A | 6/1967 | Provisor |
| 3,385,300 A | 5/1968 | Holter |
| 3,409,013 A | 11/1968 | Berry |
| 3,587,115 A | 6/1971 | Shiley |
| 3,635,223 A | 1/1972 | Klieman |
| 3,671,979 A | 6/1972 | Moulopoulos |
| 3,674,014 A | 7/1972 | Tillander |
| 3,692,018 A | 9/1972 | Goetz et al. |
| 3,755,823 A | 9/1973 | Hancock |
| 3,766,924 A | 10/1973 | Pidgeon |
| 3,769,960 A | 11/1973 | Robinson |
| 3,788,328 A | 1/1974 | Alley et al. |
| 3,833,003 A | 9/1974 | Taricco |
| 3,837,347 A | 9/1974 | Tower |
| 3,889,686 A | 6/1975 | Duturbure |
| 3,903,895 A | 9/1975 | Alley et al. |
| 3,915,171 A | 10/1975 | Shermeta |
| 3,963,028 A | 6/1976 | Cooley et al. |
| 3,970,090 A | 7/1976 | Loiacono |
| 3,983,879 A | 10/1976 | Todd |
| 4,000,739 A | 1/1977 | Stevens |
| 4,019,515 A | 4/1977 | Kornblum et al. |
| 4,029,104 A | 6/1977 | Kerber |
| 4,038,703 A | 8/1977 | Bokros |
| 4,056,854 A | 11/1977 | Boretos et al. |
| 4,106,129 A | 8/1978 | Carpentier et al. |
| 4,122,858 A | 10/1978 | Schiff |
| 4,154,227 A | 5/1979 | Krause et al. |
| 4,173,981 A | 11/1979 | Mortensen et al. |
| 4,204,328 A | 5/1980 | Kutner |
| 4,222,126 A | 9/1980 | Boretos et al. |
| 4,248,224 A | 2/1981 | Jones |
| 4,285,341 A | 8/1981 | Pollack |
| 4,287,892 A | 9/1981 | Schiff |
| 4,290,428 A | 9/1981 | Durand et al. |
| 4,297,749 A | 11/1981 | Davis et al. |
| 4,301,803 A | 11/1981 | Handa et al. |
| 4,302,261 A * | 11/1981 | Simkins et al. ......... 156/143 X |
| 4,304,239 A | 12/1981 | Perlin |
| 4,323,071 A | 4/1982 | Simpson et al. |
| 4,327,709 A | 5/1982 | Hanson et al. |
| 4,328,056 A | 5/1982 | Snooks |
| 4,343,048 A | 8/1982 | Ross et al. |
| 4,343,672 A | 8/1982 | Kanao |
| 4,351,341 A | 9/1982 | Goldberg et al. |
| 4,405,313 A | 9/1983 | Sisley et al. |
| 4,411,055 A | 10/1983 | Simpson et al. |
| 4,413,989 A | 11/1983 | Schjeldahl et al. |
| 4,417,576 A | 11/1983 | Baran |
| 4,430,081 A | 2/1984 | Timmermans |
| 4,439,186 A | 3/1984 | Kuhl |
| 4,441,495 A | 4/1984 | Hicswa |
| 4,451,251 A | 5/1984 | Osterholm |
| 5,314,418 A | 5/1984 | Takano et al. |
| 4,456,000 A | 6/1984 | Schjeldahl et al. |
| 4,459,977 A | 7/1984 | Pizon |
| 4,284,073 A | 8/1984 | Krause et al. |
| 4,464,175 A | 8/1984 | Altman et al. |
| 4,493,697 A | 1/1985 | Krause et al. |
| 4,496,345 A | 1/1985 | Hasson |
| 4,497,325 A | 2/1985 | Wedel |
| 4,512,762 A | 4/1985 | Spears |
| 4,527,549 A | 7/1985 | Gabbay |
| 4,531,935 A | 7/1985 | Berryessa |
| 4,531,936 A | 7/1985 | Gordon |
| 4,535,757 A | 8/1985 | Webster, Jr. |
| 4,540,399 A | 9/1985 | Litzie et al. |
| 4,552,558 A | 11/1985 | Muto |
| 4,573,966 A | 3/1986 | Weikl et al. |
| 4,574,803 A | 3/1986 | Storz |
| 4,577,543 A | 3/1986 | Wilson |
| 4,580,568 A | 4/1986 | Gianturco |
| 4,592,340 A | 6/1986 | Boyles |
| 4,596,552 A | 6/1986 | DeVries |
| 4,601,706 A | 7/1986 | Aillon |
| 4,601,713 A | 7/1986 | Fuqua |
| 4,610,661 A | 9/1986 | Possis et al. |
| 4,612,011 A | 9/1986 | Kautzky |
| 3,416,531 A | 12/1986 | Edwards |
| 4,631,052 A | 12/1986 | Kensey |
| 4,639,252 A | 1/1987 | Kelly et al. |
| 4,648,384 A | 3/1987 | Schmukler |
| 4,664,125 A | 5/1987 | Pinto |
| 4,665,604 A | 5/1987 | Dubowik |
| 4,681,117 A | 7/1987 | Brodman et al. |
| 4,686,085 A | 8/1987 | Osterholm |
| 4,689,041 A | 8/1987 | Corday et al. |
| 4,692,148 A | 9/1987 | Kantrowitz et al. |
| 4,697,574 A | 10/1987 | Karcher et al. |
| 4,705,507 A | 11/1987 | Boyles |
| 4,714,460 A | 12/1987 | Calderon |
| 4,721,109 A | 1/1988 | Healey |
| 4,722,347 A | 2/1988 | Abrams et al. |
| 4,723,550 A | 2/1988 | Bales et al. |
| 4,723,936 A | 2/1988 | Buchbinder et al. |
| 4,733,665 A | 3/1988 | Palmaz |
| 4,764,324 A | 3/1988 | Burnham |
| 4,741,328 A | 5/1988 | Gabbay |
| 4,751,924 A | 6/1988 | Hammerschmidt et al. |
| 4,753,637 A | 6/1988 | Horneffer |
| 4,767,409 A | 8/1988 | Brooks |
| 4,770,652 A | 9/1988 | Mahurkar |
| 4,771,777 A | 9/1988 | Horzewski et al. |
| 4,777,951 A | 10/1988 | Cribier et al. |
| 4,785,795 A | 11/1988 | Singh |
| 4,787,899 A | 11/1988 | Lazarus |
| 4,787,901 A | 11/1988 | Baykut |
| 4,790,825 A | 12/1988 | Bernstein et al. |
| 4,794,928 A | 1/1989 | Kletschka |
| 4,795,439 A | 1/1989 | Guest |
| 4,796,629 A | 1/1989 | Grayzel |
| 4,798,588 A | 1/1989 | Aillon |
| 4,804,358 A | 2/1989 | Karcher et al. |
| 4,804,365 A | 2/1989 | Litzie et al. |
| 4,808,165 A | 2/1989 | Carr |
| 4,809,681 A | 3/1989 | Kantrowitz et al. |
| 4,811,737 A | 3/1989 | Rydell |
| 4,821,722 A | 4/1989 | Miller et al. |
| 4,830,849 A | 5/1989 | Osterholm |
| 4,842,590 A | 6/1989 | Tanabe et al. |
| 4,848,344 A | 7/1989 | Sos et al. |
| 4,850,969 A | 7/1989 | Jackson |
| 4,856,516 A | 8/1989 | Hillstead |
| 4,865,581 A | 9/1989 | Lundquist et al. |
| 4,877,031 A | 10/1989 | Conway et al. |
| 4,877,035 A | 10/1989 | Bogen et al. |
| 4,878,495 A | 11/1989 | Grayzel |
| 4,883,458 A | 11/1989 | Shiber |
| 4,886,507 A | 12/1989 | Patton et al. |
| 4,889,137 A | 12/1989 | Kolobow |
| 4,898,168 A | 2/1990 | Yule |
| 4,899,787 A | 2/1990 | Ouchi et al. |
| 4,902,272 A | 2/1990 | Milder et al. |
| 4,902,273 A | 2/1990 | Choy et al. |
| 4,917,667 A | 4/1990 | Jackson |
| 4,923,450 A | 5/1990 | Maeda et al. |
| 4,927,412 A | 5/1990 | Menasche |

| Patent No. | Date | Inventor(s) |
|---|---|---|
| 4,934,996 A | 6/1990 | Mohl et al. |
| 4,943,275 A | 6/1990 | Stricker |
| 4,943,277 A | 6/1990 | Bolling |
| RE33,258 E | 7/1990 | Onik et al. |
| 4,944,729 A | 7/1990 | Buckberg et al. |
| 4,950,245 A * | 8/1990 | Brown et al. ................ 604/153 |
| 4,960,412 A | 10/1990 | Fink |
| 4,966,604 A | 10/1990 | Reiss |
| 4,969,470 A | 11/1990 | Mohl et al. |
| 4,979,939 A | 12/1990 | Shiber |
| 4,985,014 A | 1/1991 | Orejola |
| 4,986,830 A | 1/1991 | Owens et al. |
| 4,990,143 A | 2/1991 | Sheridan |
| 4,994,032 A | 2/1991 | Sugiyama et al. |
| 4,994,033 A | 2/1991 | Shockey et al. |
| 5,047,041 A | 3/1991 | Samuels |
| 5,007,896 A | 4/1991 | Shiber |
| 5,009,636 A | 4/1991 | Wortley et al. |
| 5,011,468 A | 4/1991 | Lundquist et al. |
| 5,011,469 A | 4/1991 | Buckberg et al. |
| 5,011,488 A | 4/1991 | Ginsberg |
| 5,013,296 A | 5/1991 | Buckberg et al. |
| 5,015,232 A | 5/1991 | Maglinte |
| 5,021,044 A | 6/1991 | Sharkaway |
| 5,021,045 A | 6/1991 | Bucksberg et al. |
| 5,024,668 A | 6/1991 | Peters et al. |
| 5,026,366 A | 6/1991 | Leckrone |
| 5,033,998 A | 6/1991 | Corday et al. |
| 4,276,874 A | 7/1991 | Wolvek et al. |
| 5,032,128 A | 7/1991 | Alonso |
| 5,037,434 A | 8/1991 | Lane |
| 5,041,093 A | 8/1991 | Chu |
| 5,041,098 A | 8/1991 | Loiterman et al. |
| 5,049,132 A | 9/1991 | Shaffer et al. |
| 5,053,008 A | 10/1991 | Bajaj |
| 5,059,167 A | 10/1991 | Lundquist et al. |
| 5,061,257 A | 10/1991 | Martinez et al. |
| 5,069,662 A | 12/1991 | Bodden |
| 5,080,660 A | 1/1992 | Buelna |
| 5,089,015 A | 2/1992 | Ross |
| 5,112,305 A | 3/1992 | Barath et al. |
| 5,106,368 A | 4/1992 | Uldall et al. |
| 5,109,859 A | 5/1992 | Jenkins |
| 5,116,305 A | 5/1992 | Milder et al. |
| 5,125,903 A | 6/1992 | McLaughlin et al. |
| 5,152,771 A | 10/1992 | Sabbaghian et al. |
| 5,163,905 A | 11/1992 | Michael |
| 5,163,953 A | 11/1992 | Vince |
| 5,167,628 A | 12/1992 | Boyles |
| 5,171,218 A | 12/1992 | Fonger et al. |
| 5,171,232 A | 12/1992 | Castillo et al. |
| 5,176,619 A | 1/1993 | Segalowitz |
| 5,176,660 A | 1/1993 | Truckai |
| 5,181,518 A | 1/1993 | McDonagh et al. |
| 5,186,713 A | 2/1993 | Raible |
| 5,190,520 A * | 3/1993 | Fenton, Jr., et al. .......... 604/43 |
| 5,195,942 A | 3/1993 | Weil et al. |
| 5,197,952 A | 3/1993 | Marcadis et al. |
| 5,216,032 A | 6/1993 | Manning |
| 5,219,326 A | 6/1993 | Hattler |
| 5,221,255 A * | 6/1993 | Mahurkar et al. ...... 604/282 X |
| 5,226,427 A | 7/1993 | Buckberg et al. |
| 5,236,413 A | 8/1993 | Feiring |
| 5,246,007 A | 9/1993 | Frisbie et al. |
| 5,250,038 A | 10/1993 | Melker et al. |
| 5,250,069 A | 10/1993 | Nobuyoshi et al. |
| 5,254,089 A | 10/1993 | Wang |
| 5,254,097 A | 10/1993 | Schock et al. |
| 5,270,005 A | 12/1993 | Raible |
| 5,275,622 A | 1/1994 | Lazarus et al. |
| 5,290,230 A | 3/1994 | Ainsworth et al. |
| 5,290,231 A | 3/1994 | Marcadis et al. |
| 5,295,958 A | 3/1994 | Shturman |
| 5,300,025 A | 4/1994 | Wantink |
| 5,304,132 A | 5/1994 | Jang |
| 5,308,320 A | 5/1994 | Safar et al. |
| 5,312,344 A | 5/1994 | Grinfeld et al. |
| 5,322,500 A | 6/1994 | Rickerd |
| 5,322,509 A | 6/1994 | Rickerd |
| 5,324,260 A | 6/1994 | O'Neill et al. |
| 5,330,451 A | 7/1994 | Gabbay |
| 5,332,402 A | 7/1994 | Teitelbaum |
| 5,330,433 A | 8/1994 | Fonger et al. |
| 5,334,142 A | 8/1994 | Paradis |
| 5,334,169 A | 8/1994 | Brown et al. |
| 5,069,661 A | 12/1994 | Trudell |
| 5,370,618 A | 12/1994 | Leonhardt |
| 5,370,640 A | 12/1994 | Kolff |
| 5,374,245 A | 12/1994 | Mahurkar |
| 5,380,282 A | 1/1995 | Burns |
| 5,382,239 A | 1/1995 | Orr et al. |
| 5,383,854 A | 1/1995 | Safar et al. |
| 5,385,548 A | 1/1995 | Williams et al. |
| 5,395,330 A | 3/1995 | Marcadis et al. |
| 5,395,331 A | 3/1995 | O'Neill et al. |
| 5,397,306 A | 3/1995 | Nohuyoshi et al. |
| 5,397,351 A | 3/1995 | Pavcnik et al. |
| 5,411,027 A | 5/1995 | Wiklund et al. |
| 5,411,479 A | 5/1995 | Bodden |
| 5,411,552 A | 5/1995 | Andersen et al. |
| 5,415,634 A * | 5/1995 | Glynn et al. ............ 604/282 X |
| 5,421,825 A | 6/1995 | Farcot |
| 5,423,745 A | 6/1995 | Todd et al. |
| 5,425,708 A | 6/1995 | Nasu |
| 5,428,070 A | 6/1995 | Cooke et al. |
| 5,429,597 A | 7/1995 | DeMello et al. |
| 5,433,700 A | 7/1995 | Peters |
| 5,433,446 A | 8/1995 | Shturman |
| 5,437,633 A | 8/1995 | Manning |
| 5,439,443 A | 8/1995 | Miyata et al. |
| 5,439,720 A * | 8/1995 | Choudhury ............ 156/73.2 X |
| 5,451,207 A | 9/1995 | Yock |
| 5,456,665 A | 10/1995 | Postell et al. |
| 5,458,574 A | 10/1995 | MacHold et al. |
| 5,464,394 A | 11/1995 | Miller et al. |
| 5,472,435 A | 12/1995 | Sutton |
| 5,478,309 A | 12/1995 | Sweezer et al. |
| 5,480,424 A | 1/1996 | Cox |
| 5,487,730 A | 1/1996 | Marcadis et al. |
| 5,496,294 A * | 3/1996 | Hergenrother et al. ...... 604/282 |
| 5,499,996 A | 3/1996 | Hill |
| 5,505,698 A | 4/1996 | Booth et al. |
| 5,509,897 A | 4/1996 | Twardowski et al. |
| 5,514,236 A | 5/1996 | Avellanet et al. |
| 5,525,388 A | 6/1996 | Wand et al. |
| 5,527,292 A | 6/1996 | Adams et al. |
| 5,533,957 A | 7/1996 | Aldea |
| 5,538,513 A | 7/1996 | Okajima |
| 5,549,557 A | 8/1996 | Steinke et al. |
| 5,562,606 A | 10/1996 | Huybregts |
| 5,578,010 A | 11/1996 | Ashby |
| 5,584,803 A | 12/1996 | Sweezer et al. |
| 5,591,129 A | 1/1997 | Shoup et al. |
| 5,591,142 A | 1/1997 | Van Ep |
| 5,595,181 A | 1/1997 | Hubbard |
| 5,597,377 A | 1/1997 | Aldea et al. |
| 5,599,329 A | 2/1997 | Gabbay |
| 5,658,264 A * | 8/1997 | Samson ..................... 604/282 |
| 5,695,457 A * | 12/1997 | St. Goar et al. ................ 604/4 |
| 5,697,905 A | 12/1997 | d'Ambrosio |
| 5,702,373 A | 12/1997 | Samson |
| 5,728,063 A * | 3/1998 | Preissman et al. .......... 604/282 |

| | | | | |
|---|---|---|---|---|
| 5,755,704 A | * | 5/1998 | Lunn | 604/282 |
| 5,863,366 A | * | 1/1999 | Snow | 156/143 |
| 5,879,499 A | * | 3/1999 | Corvi | 156/175 |

FOREIGN PATENT DOCUMENTS

| | | | | |
|---|---|---|---|---|
| EP | 0 238 106 | | 9/1987 | |
| EP | 0277366 | | 8/1988 | |
| EP | 0 277 367 | | 8/1988 | |
| EP | 0 321 614 | | 6/1989 | |
| EP | 0 350 302 | | 7/1989 | |
| EP | 0 357 003 | | 3/1990 | |
| EP | 0 414 350 | | 6/1990 | |
| EP | 473045 | * | 3/1992 | 604/282 |
| GB | 1097881 | | 3/1965 | |
| GB | 1097882 | | 3/1965 | |
| GB | 1284701 | | 4/1971 | |
| GB | 1414344 | | 5/1973 | |
| GB | 1467976 | | 3/1974 | |
| GB | 1477665 | | 4/1974 | |
| GB | 1513918 | | 8/1975 | |
| GB | 2056023 | | 3/1981 | |
| SU | 1271508 | | 11/1986 | |
| SU | 1371701 | | 2/1988 | |
| WO | WO 81/03613 | | 12/1981 | |
| WO | WO 83/03204 | | 9/1983 | |
| WO | WO 89/10155 | | 11/1989 | |
| WO | WO 91/01689 | | 2/1991 | |
| WO | WO 91/08791 | | 6/1991 | |
| WO | WO 91/10456 | | 7/1991 | |
| WO | WO 91/17720 | | 11/1991 | |
| WO | WO 92/17118 | | 10/1992 | |
| WO | WO 93/07927 | | 10/1992 | |
| WO | WO 95/05860 | | 2/1995 | |
| WO | WO 95/30447 | | 11/1995 | |
| WO | WO 96/33763 | | 10/1996 | |

OTHER PUBLICATIONS

Corday et al., "Symposium on the Present Status of Reperfusion of the Acutely Ischemic Myocardium. Part I," *J. Am Coll Cardiol*, 1983; 1(4):1031–1036.

Cosgrove, "Management of the Calcified Aorta: An Alternative Method of Occlusion," *Ann Thorac Surg*, 1983;36:718–719.

Crooke et al., "Biventricular Distribution of Cold Blood Cardioplegic Solution Administered by Different Retrograde Techniques," *J Cardiac Thorac Surg*, 1991;102(4):631–636.

Datascope FDA 510(k) Application, "Percluder–DL Occluding Balloon," Oct. 12, 1993.

Derwent Abstract No. 87–190867/27 (1987), SU 127508 (Gorki Kirov Medical Ins.).

DLP, Inc., Directions for Use: Cardioplegic Pressure Cannula with Vent Line, Code #14009 9 Gauge (no date).

DLP Medtronic Alternative Access Cannulae Brochure, © 1995.

DLP Worldwide Medical Innovations, Instrument Listings, pp. 5–9.

Douville et al., "Retrograde Versus Antegrade Cardioplegia: Impact on Right Ventricular Function," *Ann Thorac Surg*, 1992; 54:56–61.

Drinkwater et al., "The Use of Combined Antegrade–Retrograde Infusion of Blood Cardioplegic Solution in Pediatric Patients Undergoing Heart Operations," *Thorac and Cardiovascular Surg*, 1992; 104(5):1349–1355.

Elecath, "Bain Coronary Sinus Flow Catheter for Jugular Entry," Catalog No. 75–2337, 1994.

Erath and Stoney, "Balloon Catheter Occlusion of the Ascending Aorta," *Ann Thorac Surg*, 1983;35:560–561.

Farcot et al., "New Catheter–Pump System for Diastolic Synchronized Coronary Sinus Retroperfusion (D.S.R.)," *Med Prog Technol*, 1980; 8(1):29–37.

Farcot et al., "Synchronized Retroperfusion of Coronary Veins for Circulatory Support of Jeopardized Ischemic Myocardium," *Am J Cardiol*, 1978; 41:1101–1201.

Foster and Threlkel, "Proximal Control of Aorta with a Balloon Catheter," *Surg Gynecology & Obstetrics*, 1971, pp. 693–694.

Gundry et al., "A Comparison of Retrograde of Cardioplegia Versus Antegrade Cardioplegia in the Presence of Coronary Artery Obstruction," *Ann Thorac Surg*, 1984; 38(2):124–127.

Gundry, "Modification of Myocardial Ischemic in Normal and Hypertrophied Hearts Utilizing Diastolic Retroperfusion of the Coronary Veins," *J Thorac Cardiovasc Surg*, 1982;83:659–669.

Haendchen et al., "Prevention of Ischemic Injury and Early Reperfusion Derangements by Hypothermic Retroperfusion," *J Am Coll Cardiol*, 1983; 1(4):1067–1080.

Hammond et al., "Retrograde Coronary Sinus Perfusion: A Method of Myocardial Protection in the Dog During Left Coronary Artery Occlusion," *Ann Surg*, 1967; 166(1):139–147.

Ishizaka, "Myocardial Protection by Retrograde Cardiac Perfusion with Cold Modified Krebs Solution through Coronary Sinus During Complete Ischemic Arrest for 120 Minutes, " *J Jpn Assn Thorac Surg*, 1977;25(12);:1592–1601.

Kalmbach et al., "Cardioplegia Delivery by Combined Aortic Root and Coronary Sinus Perfusion," *Ann Thorac Surg*, 1989; 47:316–317.

Kar and Nordlander, "Coronary Veins: An Alternate Route to Ischemic Myocardium," *Heart and Lung*, Mar. 1992, vol. 21, No. 2, pp. 148–155.

Leggett et al., "Fiberoptic Cardioscopy Under Cardiopulmonary Bypass: Potential for Cardioscopy Surgery?" *Ann Thorac Surg*, 1994;58:222–225.

Lust et al., "Improved Protection of Chronically Inflow–limited Myocardium with Retrograde Coronary Sinus Cardioplegia," *Circulation III*, 1988;78(5):217–223.

Markov et al., "Reversal of Acute Myocardial Ischemia in Closed Chest Animals by Retrograde Perfusion of the Coronary Sinus with Arterial Blood," *Acta Cardiologica*, 1976; XXXI(3):185–199.

Medex, Inc., MX220 Single Tuohy–Borst Adaptor: Instructions of or Use, 1992.

Medi–Tech, Boston Scientific Corporation, "Occlusion Balloon Catheters: Instructions for Use," Rev. Jun., 1991.

Medtronic Bio–Medicus, Inc., "Bio_Medicus Cannula Instructions for Use Manual, Sterile and Non–Pyrogenic Single–Use Only," PN 85281 Rev C(10–91).

Medtronic Bio–Medicus, Inc., "Bio_Medicus Cannula Introducer Instructions for Use Manual," PN 85146–Rev. C(Jun. 1991).

Medtronic Bio–Medicus Femoral Cannulae advertisement, © 1991.

Medtronic Bio–Medicus Pediatric Cannulae advertisement, © 1991.

Medtronic Bio–Medicus Percutaneous Cannula Kits advertisements, © 1991.

Meerbaum et al., "Diastolic Retroperfusion of Acutely Ischemic Myocardium," *Am J Cardiol*, 1976; 37:588–598.

Meerbaum et al., "Hypothermic Coronary Venous Phased Retroperfusion: A Closed–Chest Treatment of Acute Regional Myocardial Ischemia," *Circulation*, 1982; 65(7): 1435–1445.

Meerbaum et al., "Retrograde Lysis of Coronary Artery Thrombus by Coronary Venouse Strepokinase Administration," *J Am Coll Cardiol*, 1983; 1(5):1262–1267.

Menasche et al., "Cardioplegia by Way of the coronary Sinus for Valvular and Coronary Surgery, " *JACC*, 1991; 18(2):628–636.

Menasche et al., "Retrograde Cardioplegia through the Coronary Sinus," *Ann Thorac Surg*, 1987; 44:214–216.

Menasche et al., "Retrograde Coronary Sinus Cardioplegia for Aortic Valve Operations: A Clinical Report on 500 Patients," *Ann Thorac Surg*, 1990; 49:556–564.

Menasche et al., "Retrograde Warm Blood Cardioplegia Preserves Hypertrophied Myocardium: A Clinical Study," *Ann Thorac Surg*, 1994; 57:1429–1435.

"Valvular Heart Disease," Merck Manual of Diagnosis and Therapy, sixteenth ed, 1992, pp. 546–553.

Ogawa, K. "Aortic Arch Reconstruction Without Aortic Cross–Clamping Using Separate Extracorporeal Circulation," *J Jpn Assn Thorac Surg*, 1993; pp. 2185–2190.

Okita et al., "Utilization of Triple–Lumen Balloon Catheter for Occlusion of the Ascending Aorta During Distal Aortic Surgery with Hypothermic Retrograde Cerebral Circulation Technique Through Left Thoracotomy," *Journal of Cardiac Surgery*, 1996; 10:699–701.

Peters, W. S., "The Promise of Cardioscopic Surgery," *AustralAs J Cardiac Thorac Surg*, 1993; 2(3):152–154.

Pilling Surgical Instruments, Vascular Clamps –Cooley Brochure, p. 385 (no date).

Razi, D..M., "The Challenge of Calcific Aortitis," *J Cardiac Surg*, 1993; 8:102–107.

Research Medical, Inc., Cardioplegia Products, Product Catalog 1995.

Research Medical, Inc., Fem Flex Femoral Percutaneous Cannulae, advertisement, *Ann Thorac Surg*, Jan., 1995, p. A38.

Research Medical, Inc. Product Catalog 1995, Cardioplegia Products.

Ropchan et al., "Salvage of Ischemic Myocardium by Non-synchronized Retroperfusion in the Pig," *The Journal of Thoracic and Cardiovascular Surgery*, Sep. 1992, vol. 104, No. 3, pp. 619–625.

Rossi, "Long–term Cardiopulmonary Bypass by Peripheral Cannulation in a Model of Total Heart Failure," *J Thorac Cardiac Vasc Surg*, 1990;100:914–921.

Sabiston, D.C., Textbook of Surgery, $10^{th}$ Ed., 1972, pp. 2021–2023, 2114–2121.

Sakaguchi et al, "Aortic Valve Replacement and Coronary Artery Bypass," *J Jpn Assoc for Thoracic Surg*, 1993;41(6):1063–1068.

Shumway, "Forward Versus Retrograde Coronary Perfusion for Direct Vision Surgery of Acquired Aortic Valvular Disease," *J Thoracic and Cardiovasc Surg*, 1959; 75–80.

Takahashi, M., "Retrograde Coronary Sinus Perfusion for Myocardial protection in Aortic A valve Surgery," *J Jpn Assn Thorac Surg*, 1982;30(3):306–318.

Uchida et al, "Percutaneous Cardiomyotomy ad Valvulotomy with Angioscopic Guidance," *American Heart Journal*, 1991;121 (4, part I):1221–1224.

Uchida et al., "Percutaneous Fiberoptic Angioscopy of the Cardiac Valves," *Am Heart J*, 1991;121(6, part I):1791–1798.

Yamaguchi, A., "A Case of Reoperation Using a Balloon Catheter with Blocked Pars Ascendes Aortae," *Kyobu Geka*, 1991; 42(11):961–964.

* cited by examiner

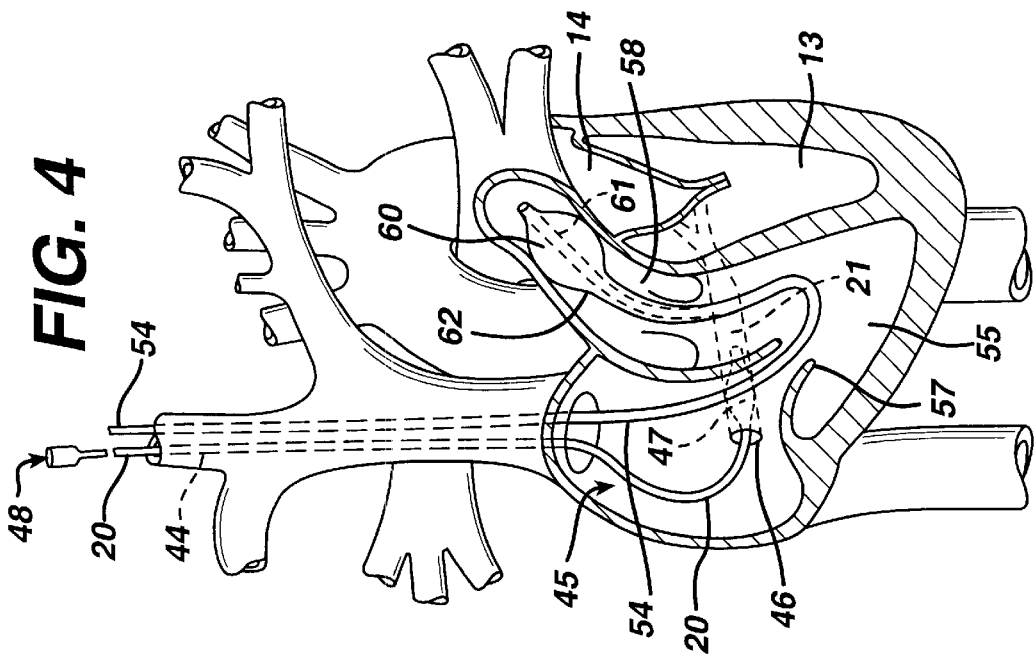
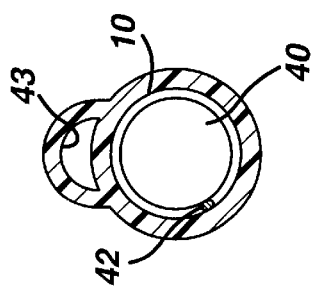
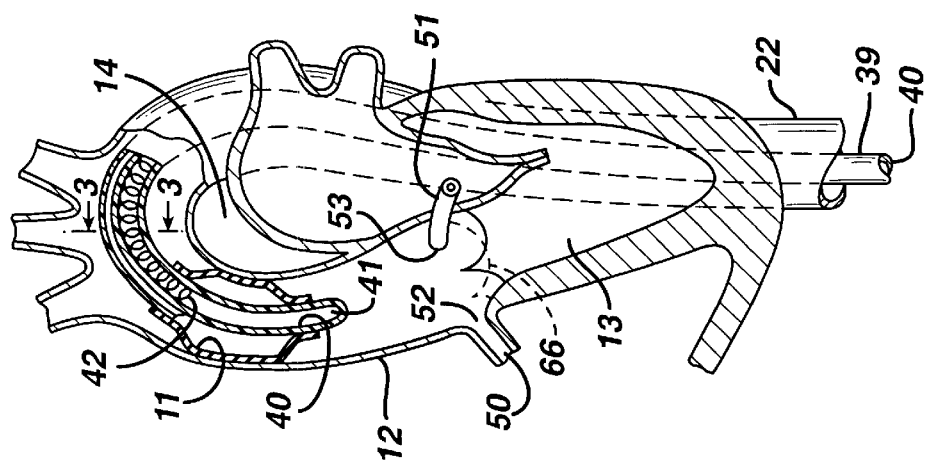

MULTI-LUMEN CATHETER

CROSS REFERENCE TO RELATED APPLICATIONS

This application is a continuation-in-part of Ser. No. 08/664,716 filed Jun. 17, 1996 and now U.S. Pat. No. 5,879,499 which is a continuation-in-part of U.S. patent application Ser. No. 08/612,230 by Snow et al., filed Mar. 7, 1996, now abandoned which is a continuation-in-part of Ser. No. 08/486,216 now U.S. Pat. No. 5,766,151, filed Jun. 7, 1995 which is a continuation-in-part of U.S. patent application Ser. No. 08/282,192, filed Jul. 28, 1994 now U.S. Pat No. 5,584,803, which is a continuation-in-part of application Ser. No. 08/162,742, filed Dec. 3, 1993, now abandoned which is a continuation-in-part of application Ser. No. 08/123,411, filed Sep. 17, 1993, now abandoned which is a continuation-in-part of application Ser. No. 07/991,188, filed Dec. 15, 1992, now abandoned which is a continuation-in-part of application Ser. No. 07/730,559, and now U.S. Pat. No. 5,370,685, filed Jul. 16, 1991. This application is also related to copending U.S. Pat. No. 05/725,496, filed Nov. 30, 1993, which is a divisional application of U.S. Pat. No. 05,433,700 which is a U.S. counterpart of Australian Patent Application No. PL 6170, filed Dec. 3, 1992. This application is also related to copending U.S. patent application Ser. No. 08/281,962, filed Jul. 28, 1994, now abandoned which is a continuation-in-part of application U.S. Pat. No. 05,571,215, filed Dec. 6, 1993, which is a continuation-in-part of application U.S. Pat. No. 5,452,733, filed Feb. 22, 1993. This application is also related to copending U.S. Pat. No. 5/735,290, filed Jul. 28, 1994, which is a continuation-in-part of U.S. Pat. No. 5/452,733, filed Feb. 22, 1993. This application is also related to copending U.S. Pat. No. 5,458,574, filed Mar. 16, 1994. The complete disclosures of all of the aforementioned U.S. patent applications and patents are hereby incorporated herein by reference for all purposes.

FIELD OF THE INVENTION

The present invention is directed to reinforced hollow tubes and their methods of manufacture and use. A specific application of the present invention is an aortic occlusion catheter for arresting a patient's heart and placing the patient on bypass.

BACKGROUND OF THE INVENTION

The present invention is directed to multi-lumen structures such as cannulae, catheters and the like. A specific application of the present invention is for an aortic occlusion catheter.

Aortic occlusion catheters are used to isolate the patient's coronary arteries from the rest of the arterial system and deliver a cardioplegic fluid to the coronary arteries to arrest heart contractions. Once the patient's heart is stopped and the coronary arteries isolated from the rest of the arterial system, the patient is prepared for surgery on the heart and great vessels. The aortic occlusion catheter has an expandable member, typically a balloon, which is expanded in the ascending aorta to occlude the ascending aorta.

Many conventional catheters are formed by extrusion methods. A problem with conventional extruded catheters is that the catheters can be prone to kinking. Kinking is particularly problematic when the catheter bends around tight-radius curves. Another problem with conventional extruded catheters is that the catheters can be relatively stiff.

SUMMARY OF THE INVENTION

The present invention solves several problems with conventional extruded catheters by providing a reinforcing catheter with increased kink resistance. The reinforced catheter of the present invention is also flexible so that trauma to the patient is minimized and so that the catheter is bent easily around structures such as the aortic arch.

The aortic occlusion catheter is preferably a multi-lumen catheter with the reinforcing member winding around at least one of the lumens in a helical manner.

The catheter also preferably includes an inflation lumen which is not positioned within the helically wound reinforcing coil. The inflation lumen is used to inflate the balloon. An advantage of positioning the inflation lumen outside the reinforcing coil is that the lumen may be easily pierced to provide an inflation outlet for delivering the inflation fluid to the balloon.

These and other aspects of the invention will become apparent with the following description of the preferred embodiments.

BRIEF DESCRIPTION OF THE DRAWINGS

FIG. 2 is a schematic partly cut-away representation of a patient's heart with the endoaortic partitioning catheter placed within the ascending aorta.

FIG. 3 is a transverse cross-sectional view of the catheter shown in FIG. 2 taken along the lines 3—3.

FIG. 4. is an enlarged view, partially in section, of the retrograde cardioplegia delivery catheter and the pulmonary venting catheter shown in FIG. 1.

DETAILED DESCRIPTION OF THE INVENTION

The invention provides a multi-lumen catheter, cannula or the like for introduction into a patient. A specific application of the present invention if for an endovascular catheter for occluding the ascending aorta and arresting the heart. Although a specific application of the present invention is for a multi-lumen aortic catheter, it is understood that the invention may be used in any other catheter, cannula or the like.

The aortic occlusion catheter is useful in performing a variety of cardiovascular, pulmonary, neurosurgical, and other procedures. The procedures include repair or replacement of aortic, mitral, and other heart valves, repair of septal defects, pulmonary thrombectomy, electrophysiological mapping and ablation, coronary artery bypass grafting, angioplasty, atherectomy, treatment of aneurysms, myocardial drilling and revascularization, as well as neurovascular and neurosurgical procedures.

The aortic occlusion catheter is especially useful in conjunction with minimally-invasive cardiac procedures, in that it allows the heart to be arrested and the patient to be placed on cardiopulmonary bypass using only endovascular devices, obviating the need for a thoracotomy or other large incision.

Figure 1:
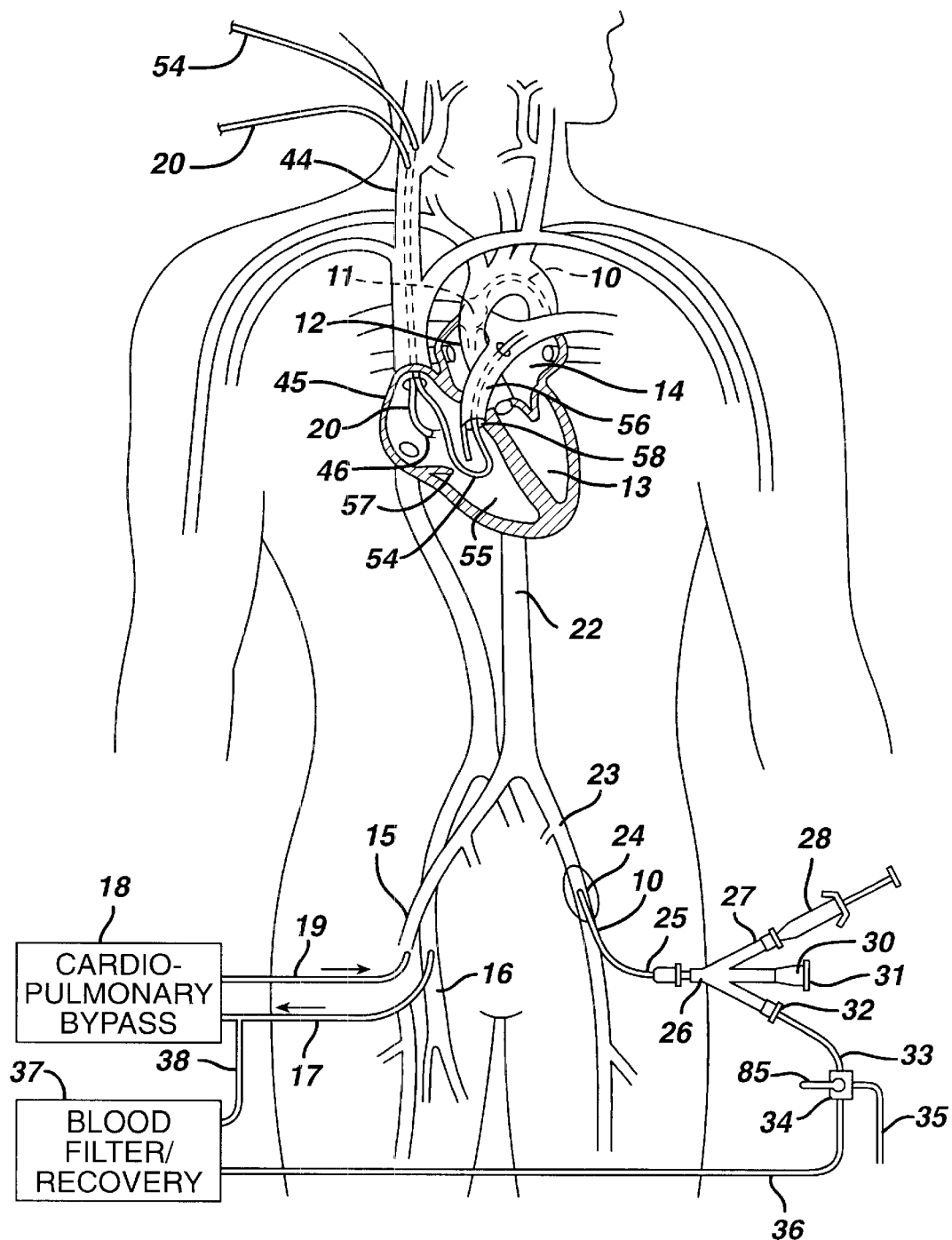
FIG. 1 schematically illustrates a cardiac access system employing an endoaortic partitioning catheter.

Reference is made to FIG. 1 which schematically illustrates a cardiac accessing system and the individual components thereof. The system includes an elongated aortic occlusion or endoaortic partitioning catheter 10 which has an expandable member 11 on a distal portion of the catheter which, when inflated as shown, occludes the ascending aorta 12 to separate or partition the left ventricle 13 and upstream portion of the ascending aorta from the rest of the patient's arterial system and securely positions the distal end of the catheter within the ascending aorta. A cardiopulmonary bypass system 18 removes venous blood from the femoral vein 16 through the blood withdrawal catheter 17 as shown, removes $CO_2$ from the blood, oxygenates the blood, and then returns the oxygenated blood to the patient's femoral artery 15 through the return catheter 19 at sufficient pressure so as to flow throughout the patient's arterial system except for the portion blocked by the expanded occluding member 11 on the aortic occluding catheter 10. The aortic occluding catheter 10 has an infusion lumen 40 for antegrade delivery of a fluid containing cardioplegic agents directly into the aortic root 12 and subsequently into the coronary arteries 52, 53 (shown in FIG. 2) to paralyze the patient's myocardium. Optionally, a retrograde cardioplegia balloon catheter 20 may be disposed within the patient's venous system with the distal end of the catheter extending into the coronary sinus 21 (shown in FIG. 4) to deliver a fluid containing cardioplegic agents to the myocardium in a retrograde manner through the patient's coronary venous system to paralyze the entire myocardium.

The elongated occluding catheter 10 extends through the descending aorta to the left femoral artery 23 and out of the patient through a cut down 24. The proximal extremity 25 of the catheter 10 which extends out of the patient is provided with a multi-arm adapter 26 with one arm 27 adapted to receive an inflation device 28. The adapter 26 is also provided with a second arm 30 with main access port 31 through which passes instruments, a valve prosthesis, an angioscope, or to direct blood, irrigation fluid, cardioplegic agents and the like to or from the system. A third arm 32 is provided for monitoring aortic root infusion pressure at the distal end of the catheter and/or for directing blood, irrigation fluid, and the like to or from the system. In the system configuration of FIG. 1, the third arm 32 of the multi-arm adapter 26 is connected to a cardiopulmonary bypass line 33 to vent the patient's heart, particularly the left ventricle, and to recover the blood removed and return it to the patient via the cardiopulmonary bypass system. A suitable valve 34 is provided to open and close the bypass line 33 and direct the fluid passing through the bypass line to a discharge line 35 or a line 36 to a blood filter and recovery unit 37. A return line may be provided to return any filtered blood to the cardiopulmonary bypass system 18 or other blood conservation system.

The details of the aortic occlusion catheter 10 and the disposition of the distal extremity thereof within the aorta are best illustrated in FIGS. 2 and 3. As indicated, the catheter 10 includes an elongated catheter shaft 39 which has a first inner lumen 40 for infusion of a cardioplegic agent in fluid communication with the main access port 31 in the second arm of the adapter 26. Additionally, the infusion lumen 40 may be adapted to facilitate the passage of instruments, a valve prosthesis, an angioscope, irrigation fluid, and the like therethrough and out the distal port 41 in the distal end thereof. A supporting coil 42 may be provided in the distal portion of the first inner lumen 40 to prevent the catheter shaft 39 from kinking when it straightened for initial introduction into the arterial system or when it is advanced through the aortic arch. The shaft 39 is also provided with a second inner lumen 43 which is in fluid communication with the interior of the occluding balloon 11.

In one embodiment of the system, a retrograde cardioplegia balloon catheter 20, which is shown in more detail in FIG. 4, is introduced into the patient's venous system through the right internal jugular vein 44 and is advanced through the right atrium 45 and into the coronary sinus 21 through the coronary sinus discharge opening 46 in the right atrium. The retrograde catheter 20 is provided with a balloon 47 on a distal portion of the catheter 20 which is adapted to occlude the coronary sinus 21 when inflated. A liquid containing a cardioplegic agent, e.g an aqueous KCl solution, is introduced into the proximal end 48 of the catheter 20, which extends outside of the patient, under sufficient pressure so that the fluid containing the cardioplegic agent can be forced to pass through the coronary sinus 21, through the capillary beds (not shown) in the patient's myocardium, through the coronary arteries 50 and 51 and ostia 52 and 53 associated with the respective coronary arteries into the blocked off portion of the ascending aorta 12 as shown. Retrograde delivery catheters are disclosed in U.S. Pat. No. 5,558,644 which is incorporated herein by reference.

A pulmonary venting catheter 54 is also shown in FIG. 4 disposed within the right internal jugular vein 44 and extending through the right atrium 45 and right ventricle 55 into the pulmonary trunk 56. Alternatively, the pulmonary venting catheter 54 may be introduced through the left jugular. The catheter 54 passes through tricuspid valve 57 and pulmonary valve 58. An inflatable occluding balloon 60 may be provided as shown on a distal portion of the pulmonary venting catheter 54 which is inflated to occlude the pulmonary trunk 56 as shown. The pulmonary venting catheter 54 has a first inner lumen 61 which extends from the distal end of the catheter to the proximal end of the catheter which vents fluid from the pulmonary trunk 56 to outside the patient's body either for discharge or for passage to the blood recovery unit and thereby decompresses the left atrium 14 through the pulmonary capillary beds (not shown). The catheter 54 has a second inner lumen 62 which is adapted to direct inflation fluid to the interior of the inflatable balloon 60.

To set up the cardiac access system, the patient is initially placed under light general anesthesia. The withdrawal catheter 17 and the return catheter 19 of the cardiopulmonary bypass system 18 are percutaneously introduced into the right femoral vein 16 and the right femoral artery 15, respectively. An incision 24 is also made in the left groin to expose the left femoral artery 23 and the aortic occluding catheter 10 is inserted into the left femoral artery through an incision therein and advanced upstream until the balloon 11 on the distal end of the occluding catheter 10 is properly positioned in the ascending aorta 12. Note that bypass could similarly be established in the left groin and the aortic occlusion catheter put into the right femoral artery. The retrograde perfusion catheter 20 is percutaneously inserted by a suitable means such as the Seldinger technique into the right internal jugular vein 44 or the subdlavian vein and advanced into the right atrium 45 and guided through the discharge opening 46 into the coronary sinus.

The pulmonary venting catheter 54 is advanced through the right or left internal jugular vein 44 or the subclavian vein (whichever is available after introduction of retrograde perfusion catheter 20) into the right atrium 45, right ventricle 55, and into the pulmonary trunk 56. The occluding balloon 60 may be inflated if necessary by inflation with fluid passing through the lumen 62 to block the pulmonary trunk 56 and vent blood therein through the lumen 61 where it is discharged through the proximal end of the catheter which extends outside of the patient. Alternatively, the occluding balloon 60 may be partially inflated with air or $CO_2$ during introduction for flow-assisted placement. The venting of the pulmonary trunk 56 results in the decompressing of the left atrium 14 and, in turn, the left ventricle. In the alternative, the venting catheter 54 may be provided with means on the exterior thereof, such as expanded coils as described in U.S. Pat. No. 4,889,137 (Kolobow), which hold open the tricuspid and pulmonary valves and perform the same function of decompressing the left atrium. See also the article written by F. Rossi et. al. in the Journal of Thoracic Cardiovascular Surgery, 1900;100:914–921, entitled "Long-Term Cardiopulmonary Bypass By Peripheral Cannulation In A Model Of Total Heart Failure," which is incorporated herein in its entirety by reference.

The operation of the cardiopulmonary bypass unit 18 is initiated to withdraw blood from the femoral vein 16 through catheter 17, remove $CO_2$ from and add oxygen to the withdrawn blood and then pump the oxygenated blood through the return catheter 19 to the right femoral artery 15. The balloon 11 may then be inflated to occlude the ascending aorta 12, causing the blood pumped out of the left ventricle (until the heart stops beating due to the cardioplegic fluid as discussed hereinafter) to flow through the discharge port 41 into the first inner lumen 40 of the occluding catheter. The blood flows through the inner lumen 40 and out the third arm 32 of the adapter 26 into the bypass line 33 and then into the blood filter and blood recovery unit 37 through the valve 34 and line 36. For blood and irrigation fluids containing debris and the like, the position of the valve 34 may be changed to direct the fluid through the discharge line 35.

In a first embodiment of the method, a liquid containing a cardioplegic agent such as KCl is directed through the infusion lumen 40 of the catheter 10 into the aortic root 12 and subsequently into the coronary arteries 52, 53 to paralyze the patient's myocardium. Alternatively, if a retroperfusion catheter 20 is provided for delivery of the cardioplegic agent, the balloon 47 on the distal extremity of the catheter 20 is inflated to occlude the coronary sinus 21 to prevent fluid loss through the discharge opening 46 into the right atrium 45. A liquid containing a cardioplegic agent such as KCl is directed through the catheter 20 into the coronary sinus 21 and the pressure of the cardioplegic fluid within the coronary sinus 21 is maintained sufficiently high, (e.g. 40 mm Hg) so that the cardioplegic fluid will pass through the coronary veins, crossing the capillary beds to the coronary arteries 50 and 51 and out the ostia 52 and 53. The cardioplegic fluid pressure within the coronary sinus 21 should be maintained below 75 mm Hg to avoid pressure damage to the coronary sinus 21. Once the cardioplegic fluid passes through the capillary beds in the myocardium, the heart very quickly stops beating. At that point the myocardium is paralyzed and has very little demand for oxygen and can be maintained in this state for long periods of time with minimal damage.

With the cardiopulmonary bypass system in operation, the heart completely paralyzed and not pumping, the left atrium and ventricle decompressed and the ascending aorta blocked by the inflated balloon 11 on the occluding catheter 10, the heart is appropriately prepared for a cardiac procedure.

Inflation of the inflatable member 11 on the distal end of the delivery catheter 10 fixes the distal end of the occluding catheter 10 within the ascending aorta 12 and isolates the left ventricle 13 and the upstream portion of the ascending aorta from the rest of the arterial system downstream from the inflatable member. The passage of any debris or emboli, solid or gaseous, generated during a cardiovascular procedure to regions downstream from the site would be precluded by the inflated balloon 11. Fluid containing debris or emboli can be removed from the region between the aortic valve and the occluding balloon 11 through the inner lumen 40 of catheter 10. A clear, compatible fluid, e.g. an aqueous based fluid such as saline delivered through the inner lumen 40 or the cardioplegic fluid discharging from the coronary ostia 52 and 53, may be maintained in the region wherein the cardiovascular procedure is to be performed to facilitate use of an angioscope or other imaging means that allows for direct observation of the cardiac procedure. Preferably, the fluid pressure in the left ventricle 13 is maintained sufficiently higher than that in the left atrium to prevent blood from the left atrium from seeping into the left ventricle and interfering with the observation of the procedure. The cardiac access system described above is presented to illustrate use of the endoaortic occlusion catheter 10, however, any other catheters may be used in connection with the endoaortic occlusion catheter 10 and other aortic occlusion catheters described herein.

In a further aspect of the invention, illustrated in FIGS. 5–8, the endoaortic partitioning catheter 195 is coupled to an arterial bypass cannula 150 that is specially adapted to serve as a dual purpose arterial bypass cannula and introducer sheath so as to allow the catheter 195 and the cannula 150 to be introduced through the same arterial puncture. The arterial bypass cannula 150 is configured for connection to a cardiopulmonary bypass system for delivering oxygenated blood to the patient's arterial system. The arterial bypass cannula 150, shown in FIG. 5, has a cannula body 151 which is preferably made of a transparent, flexible, biocompatible polyurethane elastomer or similar material. In one preferred embodiment, the cannula body 151 has a 45; beveled distal end 153, a proximal end 152, a blood flow lumen 157 extending between the proximal end 152 and the distal end 153, and an outflow port 191 at the distal end 153. Alternatively, the cannula body 151 can have a straight cut distal end with chamfered or rounded edge. Optionally, a plurality of additional outflow ports may be provided along the length of cannula body 151, particularly near distal end 153. The cannula body 151 is tapered from the proximal end 152 to the distal end 153 and, in one preferred embodiment, the tapered cannula body 151 is reinforced with a coil of flat stainless steel wire 154 embedded in the wall of the cannula body 151. Adjacent to the proximal end 152 of the cannula body 151, proximal to the reinforcing coil 151, is a clamp site 151 which is a flexible section of the tubular cannula body 151 that can be clamped with an external clamp, such as a Vorse type tube occluding clamp, forming a hemostatic seal to temporarily stop blood flow through the lumen 157 of the cannula 150. In a preferred embodiment, the cannula body 151 has a length between about 10 cm and 60 cm, and preferably between about 12 cm and 30 cm. In one particular embodiment, the cannula body 151 has a distal external diameter of approximately 7 mm or 21 French (Charriere scale) and a distal internal diameter of approximately 6.0 mm or 18 French. In a second particular embodiment, the cannula body 151 has a distal external diameter of approximately 7.7 mm or 23 French (Charriere scale) and a distal internal diameter of approximately 6.7 mm or 20 French. Preferably, the proximal end 152 of the cannula body 151 of either embodiment has an internal diameter of approximately ⅜ inch or 9.5 mm. The choice of which embodiment of the arterial bypass cannula 150 to use for a given patient will depend on the size of the patient and the diameter of the artery chosen for the arterial cannulation site. Generally, patients with a larger body mass will require a higher infusion rate of oxygenated blood while on cardiopulmonary bypass, therefore the larger arterial bypass cannula 150 should be chosen if the size of the artery allows.

Figure 8:
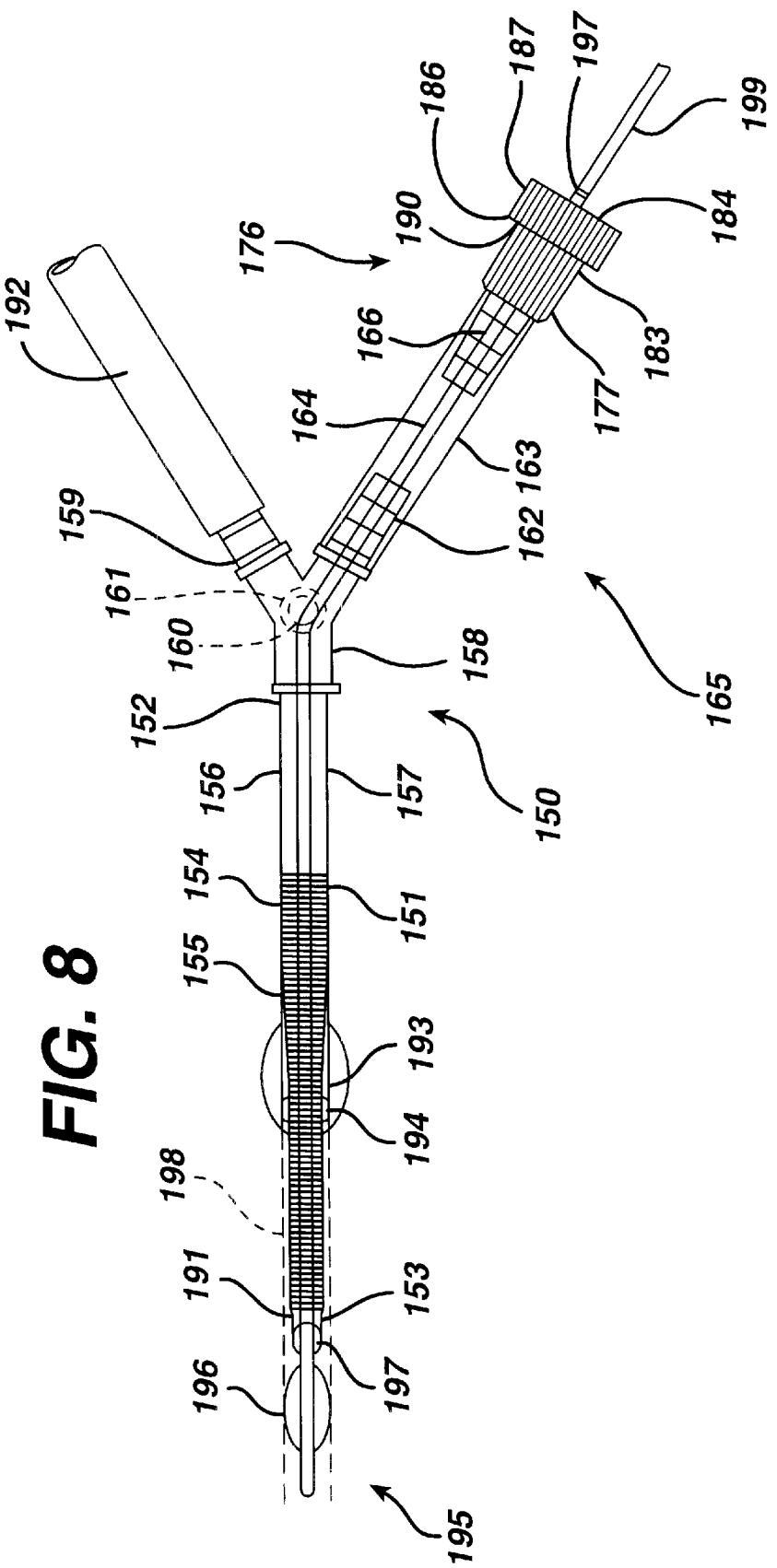
FIG. 8 illustrates the cannula of FIGS. 5 and 6 with the endoaortic partitioning catheter introduced into the patient's femoral artery.

An adapter assembly 165 is connected to the proximal end 152 of the cannula body 151. In one preferred embodiment, the adapter assembly 165 and the cannula body 151 are supplied preassembled as a single, sterile, ready-to-use unit. Alternatively, the adapter assembly 165 can be packaged and sold as a separate unit to be connected to the cannula body 151 at the point of use. The adapter assembly 165 has a Y-fitting 158 which is connected to the proximal end 152 of the cannula body 151. The Y-fitting 158 has a first branch ending in a barbed connector 159 which is configured for fluid connection to tubing 192 from a cardiopulmonary bypass system, as shown in FIG. 8. To prepare the arterial bypass cannula 150 for insertion into a peripheral artery, such as a patient's femoral artery or brachial artery, by an arterial cutdown or by a percutaneous Seldinger technique, a connector plug 171, which is molded of a soft, elastomeric material, is placed over the barbed connector 159. A tapered dilator 167 is passed through a wiper-type hemostasis seal 172 in the connector plug 171. The wiper-type hemostasis seal 172 is a hole through the elastomeric connector plug 171 that has a slight interference fit with the external adiameter of the dilator 167. A series of ridges can be molded within the hemostasis seal 172 to reduce the sliding friction on the dilator 167 while maintaining a hemostatic seal. The dilator 167 has a tapered distal tip 169, a proximal hub 170 with a luer lock connector, and a guidewire lumen 179, sized for an 0.038 inch diameter guidewire, that runs from the distal tip 169 to the proximal hub 170. The diameter of the dilator 167 is such that the dilator 167 substantially fills the cannula lumen 157 at the distal end 153 of the cannula body 151. The length of the dilator 167 is such that the distal tip 169 of the dilator 167 extends approximately 2 to 5 cm, and more preferably 4 to 5 cm, beyond the beveled end 153 of the cannula body 151 when the dilator hub 170 is against the connector plug 170. The dilator 167 may assume a bend 173 in it at the point where the dilator 167 passes through the Y-fitting 158 when the dilator 167 is fully inserted. One or more depth markers 174, 175 can be printed on the dilator 167 with a nontoxic, biocompatible ink. One depth marker 174 may be placed so that, when the marker 174 is just proximal to the hemostasis seal 172 on the elastomeric connector plug 171, the tapered distal tip 169 of the dilator 167 is just emerging from the beveled end 153 of the cannula body 151. In one particular embodiment, the tapered dilator 167 is made of extruded polyurethane with a radiopaque filler so that the position of the dilator can be verified fluoroscopically.

A second branch of the Y-fitting 158 is connected to an extension tube 162 which terminates in a hemostasis valve 176 configured to receive the endoaortic partitioning catheter 195 therethrough. The extension tube 162 has a flexible middle section which serves as a proximal clamp site 164 that can be clamped with an external clamp, such as a Vorse type tube occluding clamp, forming a hemostatic seal to temporarily stop blood flow through the lumen 163 of the extension tube 162. The lumen 163 of the extension tube 162 between the proximal clamp site 164 and the hemostasis valve 176 serves as a catheter insertion chamber 166, the function of which will be more fully explained in connection with FIG. 7.

In a preferred embodiment of the arterial bypass cannula 150, the hemostasis valve 176 is a type of compression fitting known in the industry as a Tuohy-Borst adapter. The Tuohy-Borst adapter 176 is shown in greater detail in FIG. 6. The Tuohy-Borst adapter 176 has a compressible tubular or ring-shaped elastomeric seal 183 that fits within a counterbore 179 in the fitting body 177. The elastomeric seal 183 is preferably made from a soft, resilient, self-lubricating elastomeric material, such as silicone rubber having a hardness of approximately 20–50 and preferably 40–50 Shore A durometer. The elastomeric seal 183 has a central passage 184 with a beveled entry 185 on the proximal end of the passage 184. The elastomeric seal 183 has a beveled distal surface 186 angled at about 45; which fits against a tapered seat 180 in the bottom of the counterbore 179 that is angled at about 60;. A threaded compression cap 187 screws onto the fitting body 177. The threaded cap 187 has a tubular extension 187 which fits within the counterbore 179 in the fitting body 177. An externally threaded section 188 on the proximal end of the tubular extension 187 engages an internally threaded section 181 within the proximal end of the counterbore 179. When the threaded cap 187 is screwed down onto the fitting body 177, the tubular extension 189 bears on the elastomeric seal 183 forcing it against the tapered seat 180 of the counterbore 179. The resultant force on the elastomeric seal 183 squeezes the elastomeric seal 183 inward to close off the passage central 184 to make a hemostatic seal. When the threaded cap 187 is unscrewed again from the fitting body 177, the central passage 184 of the elastomeric seal 183 opens up again. The deliberate 15; mismatch between the angle of the beveled distal surface 186 of the elastomeric seal 183 and the tapered seat 180 of the counterbore 179 prevents the elastomeric seal 183 from binding and causes the central passage 184 to open up reliably when the threaded cap 187 is unscrewed from the fitting body 187. An internal ridge 190 within the threaded cap 187 engages in a snap fit with an external ridge 182 on the proximal end of the fitting body 177 to keep the threaded cap 187 from being inadvertently separated from the fitting body 177 if the threaded cap 187 is unscrewed to the point where the threads 188, 181 are no longer engaged.

In one particular embodiment, the central passage 184 of the elastomeric seal 183 has an internal diameter of about 5 mm to allow clearance for inserting a catheter 195 with a shaft diameter of 3–4 mm through the Tuohy-Borst adapter 176 without damaging the occlusion balloon 196 mounted on it. The Tuohy-Borst adapter 176 is adjustable through a range of positions, including a fully open position for inserting the balloon catheter 196, a partially closed position for creating a sliding hemostatic seal against the shaft 197 of the catheter 195, and a completely closed position for creating a hemostatic seal with no catheter in the central passage 184. In an alternative embodiment, the central passage 184 of the elastomeric seal 183 can be sized to have a slight interference fit with the shaft 197 of the catheter 195 when uncompressed. In this embodiment, the Tuohy-Borst adapter 176 has positions which include a fully open position for creating a sliding hemostatic seal against the shaft 197 of the catheter 195, and a completely closed position for creating a hemostatic seal with no catheter in the central passage 184. In a second alternative embodiment, a separate ring-like wiper seal (not shown) is added in series with the Tuohy-Borst adapter 176 to create a passive sliding hemostatic seal against the shaft 197 of the catheter 195 without the necessity of tightening the threaded cap 187. Additionally, the Tuohy-Borst adapter 176, in either embodiment, may have a tightly closed position for securing the catheter shaft 197 with respect to the patient. In other alternative embodiments, other known hemostasis valves may be substituted for the Tuohy-Borst adapter 176 as just described.

In a particularly preferred embodiment, the internal surface of the lumen 163 of the extension tube 162 and/or the internal surface of the lumen 157 of the cannula body 151 are coated with a highly lubricious biocompatible coating, such as polyvinyl pyrrolidone, to ease the passage of the endoaortic partitioning catheter 195, and especially the occlusion balloon 196, through these lumens. Other commercially available lubricious biocompatible coatings can also be used, such as Photo-Link"coating available from BSI Surface Modification Services of Eden Prairie, Minn. sodium hyaluronate coating available from Biocoat of Fort Washington, Pa.; proprietary silicone coatings available from TUA of Sarasota, Fla.; and fluid silicone or silicon dispersions. Similarly, a distal portion of the exterior of the cannula body 151 can be coated with one of these lubricious biocompatible coatings to facilitate insertion of the arterial bypass cannula 150 into the artery at the cannulation site. Furthermore, the endoaortic partitioning catheter 195 itself, in any of the embodiments described herein, can be coated with one of these lubricious biocompatible coatings to facilitate its insertion and passage through the arterial bypass cannula 150 and the patient's vasculature. Preferably, the occlusion balloon 196 of the endoaortic partitioning catheter 195 should be free of any lubricious coating so that there is sufficient friction between the expanded occlusion balloon and the interior aortic wall to prevent accidental dislodgement or migration of the occlusion balloon 196.

Figure 5:
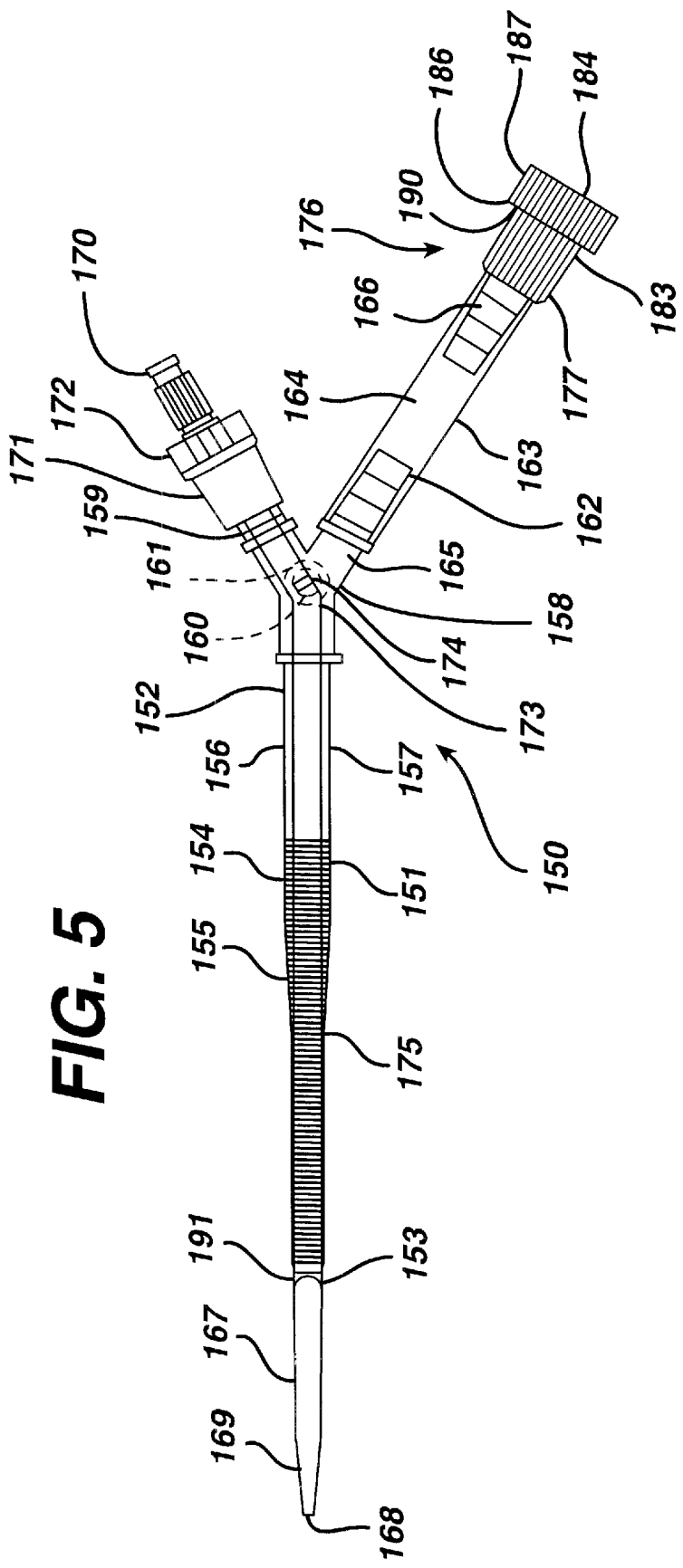
FIG. 5 is a front view of a dual function arterial cannula and introducer sheath for use with the endoaortic partitioning catheter.
Figure 6:
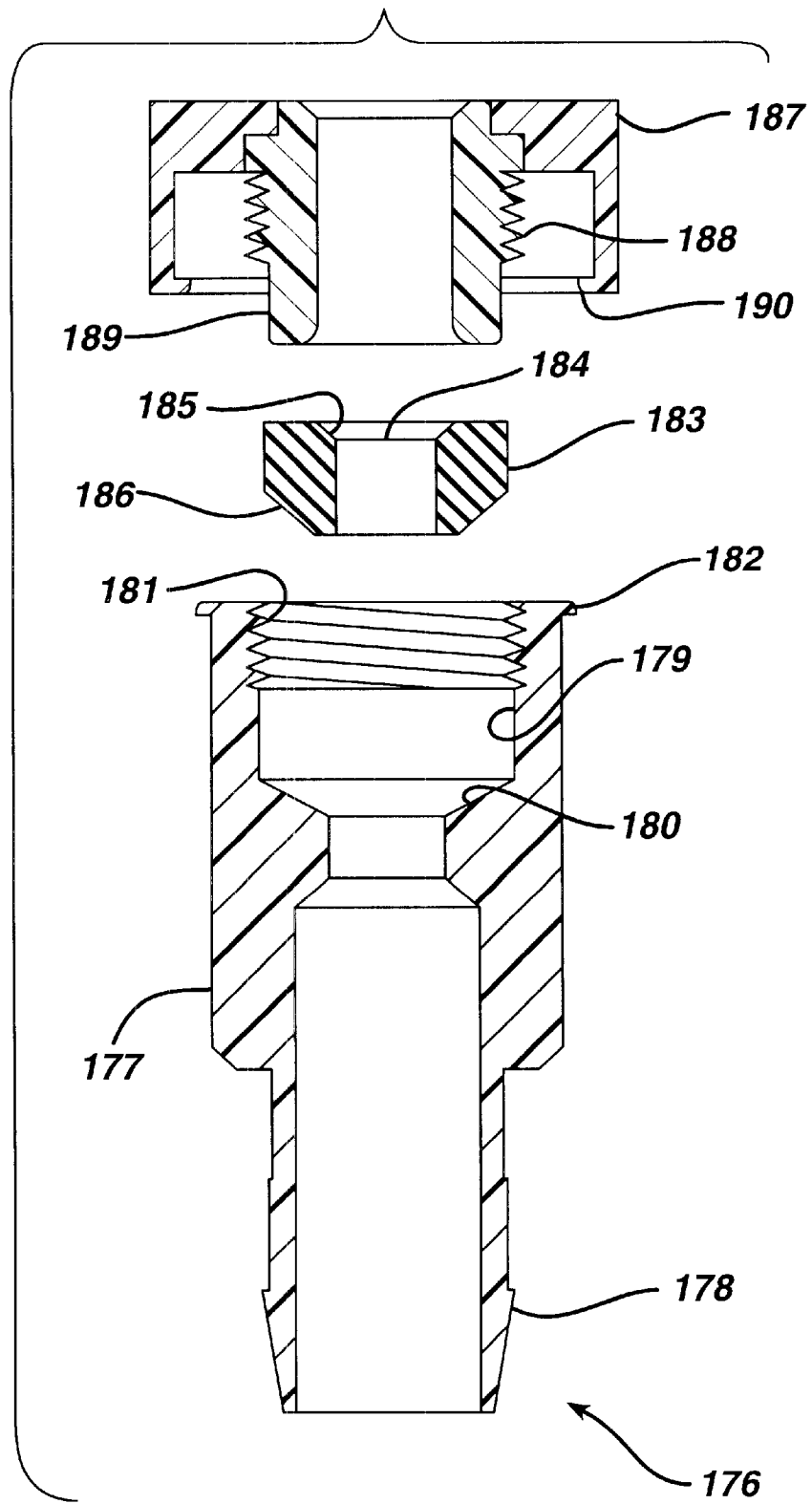
FIG. 6 is a cross sectional view of the hemostasis fitting of the dual function arterial cannula and introducer sheath.
Figure 7:
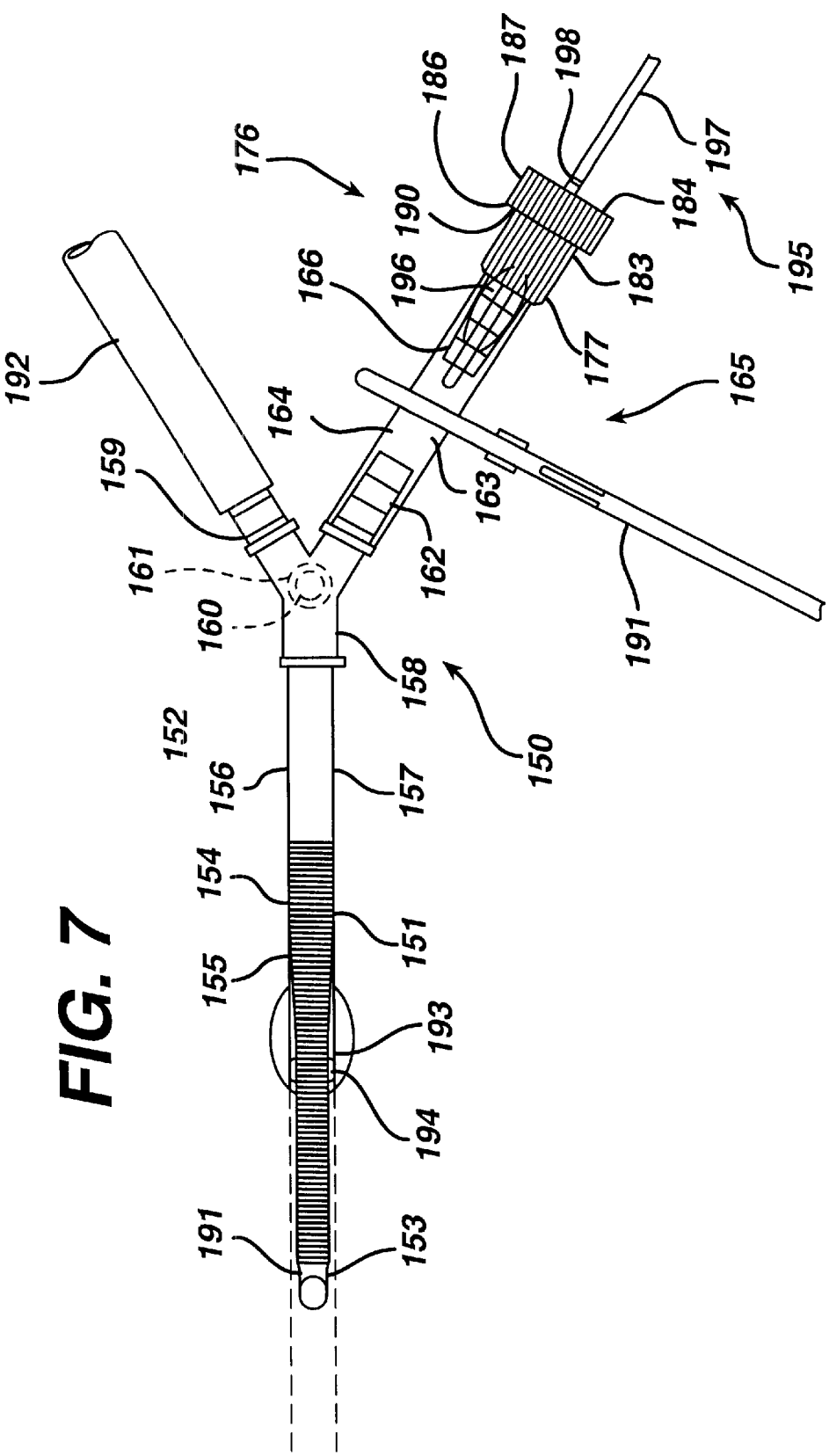
FIG. 7 illustrates the cannula of FIG. 5 with an endoaortic partitioning catheter introduced into the catheter insertion chamber.

In operation, the arterial bypass cannula 150 is prepared for insertion as shown in FIG. 5, with the tapered dilator 167 in place in the blood flow lumen 157 of the cannula body 151 and with the Tuohy-Borst fitting 176 completely closed. An arterial cutdown is made into an artery, preferably the patient's femoral artery, at the cannulation site or a guidewire is placed percutaneously using the Seldinger technique and the dilator 167 and the distal end 153 of the cannula body 151 are inserted into the lumen of the artery with the bevel up. A suture 194 can be tied around the artery 193 where the cannula body 151, as shown in FIG. 7, inserts to avoid bleeding from the artery 193 at the cannulation site. The dilator 167 is then withdrawn from the cannula body 151, allowing blood to flash back and fill the lumen 157 of the cannula body 151. When the tip 168 of the dilator 167 is proximal to the distal clamp site 156 an external clamp is applied to the distal clamp site 156 to stop further blood flow. The dilator 167 is completely withdrawn and the connector plug 171 is removed so that a tube 192 from the cardiopulmonary bypass system can be attached to the barbed connector 159 of the Y-fitting 158, as shown in FIG. 7. Air is bled from the arterial bypass cannula 150 by elevating the extension tube 162 and opening the Tuohy-Borst fitting 176 slightly and releasing the external on the distal clamp site 156 to allow the blood to flow out through the Tuohy-Borst fitting 176. Alternatively, air can be bled out of the arterial bypass cannula 150, through an optional vent fitting with a luer cap (not shown) that can be provided on the Y-fitting 158 or an infusion line and a threeway stopcock. The optional vent fitting can be also used as a port for monitoring perfusion pressure within the arterial bypass cannula 150. Once the air is bled out of the system, the external clamp can be removed from the distal clamp site 156 the cardiopulmonary bypass system pump can be turned on to perfuse the patient's arterial system with oxygenated blood at a rate of about 3 to 6 liters/minute, preferably at a pump pressure of less than about 500 mm Hg.

To introduce the endoaortic partitioning catheter 195 into the arterial bypass cannula 150, an external clamp 191 is placed on the proximal clamp site 164, as shown in FIG. 7, to stop blood from flowing out through the extension tube 162 and the Tuohy-Borst adapter 176 is opened all the way by unscrewing the threaded cap 187 to open up the passage 184 through the elastomeric seal 183. The distal end of the endoaortic partitioning catheter 195 with the occlusion balloon 196 mounted thereon is inserted through the passage 184 of the Tuohy-Borst adapter 176 into the insertion chamber 166 of the arterial bypass cannula 150. Optionally, first and second depth markers 198, 199 may be printed on the shaft 197 of the endoaortic partitioning catheter 195 with a nontoxic, biocompatible ink. The first depth marker 198 on the catheter 195 indicates when the occlusion balloon 196 is entirely distal to the elastomeric seal 183. When the first depth marker 198 is positioned just proximal to the threaded cap 187, the Tuohy-Borst adapter 176 should be tightened to create a sliding, hemostatic seal around the catheter shaft 197. Now, the clamp 191 can be removed to allow the catheter 195 to be advanced distally through the arterial bypass cannula 150.

Before the endoaortic partitioning catheter 195 enters the blood flow lumen 157 within the Y-fitting 158, the perfusion rate from the cardiopulmonary bypass system pump should be temporarily turned down to a rate of about 1 to 2 liters/minute to avoid hemolysis, tubing disruptions or other complications due to the additional flow resistance caused by the occlusion balloon 196 as it passes through the blood flow lumen 157. The catheter 195 can now be advanced distally until the occlusion balloon 986 is distal to the distal end 153 of the cannula body 151. A second depth marker 199 on the catheter 195 indicates when the occlusion balloon 196 is entirely distal to the distal end 153 of the cannula body 151. When the second depth marker 198 reaches the proximal end of the threaded cap 187, as shown in FIG. 7, the perfusion rate from the cardiopulmonary bypass system pump should be returned to a rate of about 3 to 6 liters/minute. The endoaortic partitioning catheter 195 can now be advanced into the ascending aorta for partitioning the heart and inducing cardioplegic arrest according to the methods described above. When the endoaortic partitioning catheter 195 is in position within the ascending aorta the Tuohy-Borst adapter 176 can be tightened around the catheter 195 to act as a friction lock to hold the catheter in place.

After completion of the surgical procedure on the heart, the endoaortic partitioning catheter 195 can be removed from the arterial bypass cannula 150 by reversing the sequence of operations described above. The arterial bypass cannula 150 can remain in place until the patient has been weaned from cardiopulmonary bypass, then the arterial bypass cannula 150 can be removed and the arterial puncture site repaired. The arterial bypass cannula 150 is described to illustrate the relationship between the endoaortic partitioning catheter 195 and arterial bypass cannula 150. Another preferred arterial bypass cannula is described in co-pending U.S. Pat. No. 5,863,366 entitled "Cannula and Method of Manufacture and Use," issued Jan. 26, 1999 by inventor David Snow, which is hereby incorporated by reference.

It should be noted that for the venous side of the cardiopulmonary bypass system, a similar dual purpose venous bypass cannula and introducer sheath with the above-described features can be used for accessing the femoral vein and for introducing a venting catheter or other devices into the venous side of the circulatory system. In a venous configuration the dual purpose venous bypass cannula and introducer sheath preferably has an external diameter of about 21 to 32 French units, an internal diameter of about 18 to 30 French units, and a length of about 50 to 75 cm.

Figure 9:
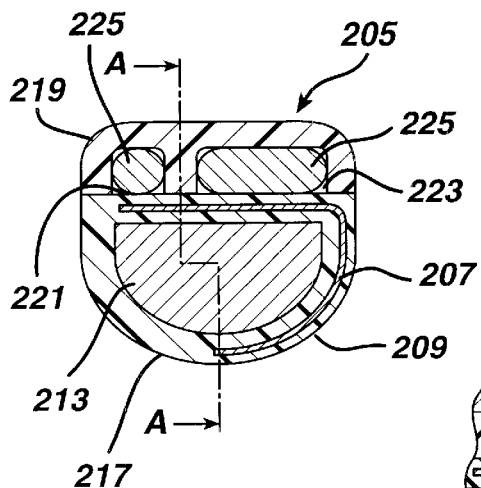
FIG. 9 is a cross-sectional view of a reinforced section for an aortic occlusion catheter.
Figure 10:
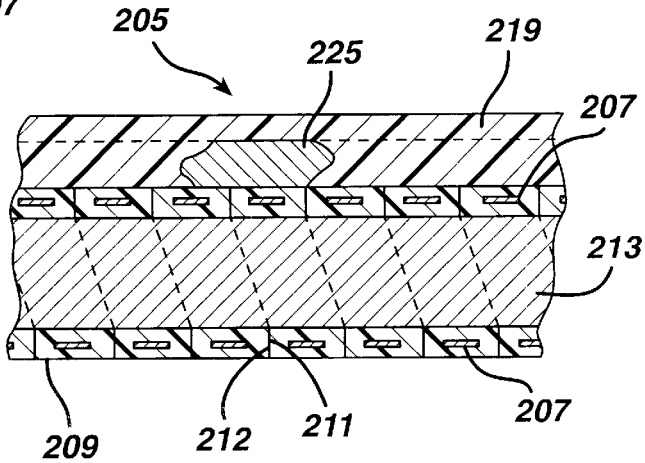
FIG. 10 is a longitudinal cross-sectional view of the construction of FIG. 9 around line A—A.

Referring to FIGS. 9 and 10, a preferred structure for a reinforced section 205 of a catheter, cannula or the like is shown. An elongate member 207 is coated with a coating 209. The coating 209 is preferably extruded over the elongate member 207 but may be applied in any other manner such as dipping. The elongate member 207 may be made of any suitable material which has the requisite structural characteristics such as stainless steel, nickel titanium or a polymer. A preferred material is stainless steel ribbon having a width of between 0.006 and 0.012 inch and a height of between 0.002 and 0.004 inch. The elongate member 207 may have any cross-sectional shape, such as circular, and a preferred cross-sectional shape is a quadrangle. Any suitable coating 209 may be used and preferred coatings include polymers and specifically polyurethane, rubber, PVC or any thermoplastic elastomer.

The coating 209 is extruded over the elongate member 207 so that the coating 209 has opposing sides 211, 212 which are configured to engage one another when the coated elongate member 207 is wrapped around a mandrel 213 M. A preferred shape is a quadrangle, however, any other shape may be used including irregular shapes so long as the opposing sides 211, 212 are configured to engage one another. The coating 209 preferably has a height of 0.006 to 0.014 inch and more preferably 0.008 to 0.012 inch and most preferably 0.008 to 0.010 inch. The coating 209 also has a length of 0.012 to 0.026 inch and more preferably 0.012 to 0.018 inch and most preferably 0.016 to 0.018 inch. The resulting thickness of the reinforced section 205 provides a thin walled tube which resists kinking.

The coated elongate member 207 is then wrapped around the mandrel 213 in a helical manner. The coated elongate member 207 is wound so that a first lumen 215 is formed when the mandrel 213 is removed. The first lumen has a D-shaped cross-sectional shape which has an arcuate portion 217 extending around at least 120 (degrees) and more preferably at least 180 (degrees). The arcuate portion 217 is preferably a segment of a circle. The mandrel 213 is preferably coated with a lubricious coating such as TFE to prevent sticking. Although the first lumen 215 is preferably D-shaped, it may take any other shape including circular or oval. Furthermore, although it is preferred to coat the elongate member 207 with the coating 209 and wind the coated elongate member 207 around the mandrel 213, the coated elongate member 207 may be formed by any other method such as dipping or coextrusion.

A member 219 is positioned on top of coated elongate member 207 after the coated elongate member 207 has been wound around the mandrel 213. The member 219 is preferably W-shaped so that second and third lumens 221, 223 are formed when the member 219 is positioned on top of the coated elongate member 207. Blockers 225, which are preferably made of Teflon, are inserted into the second and third lumens 221, 223 so that they don't collapse when the reinforced section 205 is heated as will be discussed below. Although it is preferred that the member 219 has two open channels, the member 219 may include two closed channels which for the second and third lumens 221, 223 without departing from the scope of the invention. An advantage of using the open channel design of the member 219 is that the overall size of the reinforced section 205 is minimized. The member 219 is preferably made of a polymer and a preferred polymer is preferably the same as for coating 209, however, the member 219 preferably has a higher durometer than the coating 209 so that the coating 209 provides increased bendability while the member 219 provides pushability and kink resistance. The member 219 preferably has a thickness of 0.003 to 0.010 inch and more preferably 0.005 to 0.008 inch.

Figure 11:
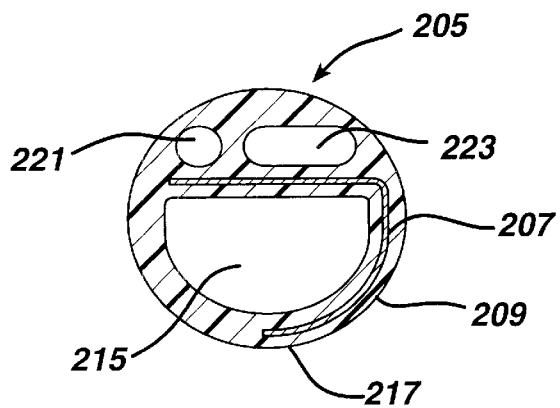
FIG. 11 is a cross-sectional view of reinforced section of FIGS. 9 and 10 after fusing together the member and coated elongate member.

A heat shrink tube (not shown) is then positioned around the coated elongate member 207 and member 219. The coated elongate member 207 and the member 219 are then heated to melt the coating 209 and member 219 so that they fuse together to form an integrated structure. Referring to FIG. 11 the reinforced section 205 is then cooled and the shrink tube, blockers 225 and mandrel 213 are removed. The resulting reinforced section 205 preferably has a circular cross-sectional shape, however, any other shape may be used. Although it is preferred to heat the coated elongate member 207 and member 219 together, a solvent may also be used to bond the two members 207, 219 together. The resulting reinforced section 205 preferably has a cross-sectional area of 0.0135 to 0.0154 inch(squared) and more preferably 0.0135 to 0.0145 inch(squared) which corresponds to an outer diameter of 0.131 to 0.140 inch and more preferably 0.131 to 0.136 inch. The resulting reinforced section 205 minimizes the size of the catheter while providing sufficient structural characteristics to prevent kinking when the catheter extends around the aortic arch. The first lumen 215 has a cross-sectional size of 0.00754 to 0.01053 inch(squared) and more preferably 0.00817 to 0.01053 inch (squared). The third lumen 223 preferably has a cross-sectional size of 0.00095 to 0.0015 inch(squared) and more preferably 0.0010 to 0.0012 inch(squared).

Figure 12:
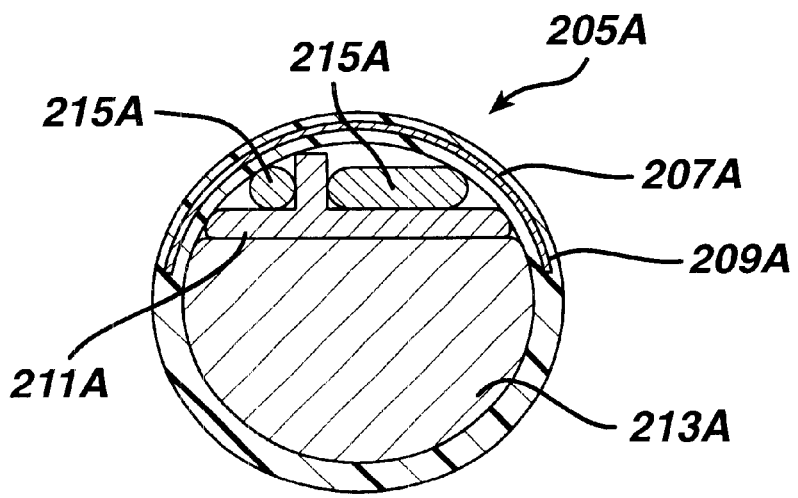
FIG. 12 is a cross-sectional view of another reinforced section having a member positioned within a coated elongate member.

Referring to FIG. 12, another reinforced section 205A is shown. The reinforced section 205A includes an elongate member 207A coated with a coating 207A. The elongate member 207A and coating 209A may be any of the elongate members and coatings described above and is preferably the same as the elongate member 207 and coating 209 of the reinforced section 205. A member 211A and blockers 215A are positioned on the member 211A. The coated elongate member 207A is then wrapped around the mandrel 213A, member 211A, and blockers 215A in a helical manner. The coated elongate member 207A preferably has the same cross-sectional shape as the coated elongate member 207 and the coated elongate member 207A is wrapped so that adjacent portions of the coated elongate member 207A engage one another in the manner described above. Although it is preferred to coat the elongate member 207A with the coating 209A and wind the coated elongate member around the mandrel 213A, member 211A and blockers 215N, the coated elongate member 207A may be formed by any other method such as dipping or coextrusion.

The member 211A is preferably T-shaped but may take any other shape which forms first, second and third lumens 219A, 221A, 223A. The blockers prevent the second and third lumens 221A, 223A from closing when the coated elongate member 207A and member 211A are fused together. A shrink tube (not shown) is positioned around the coated elongate member 207A and the coated elongate member 207A and member 211A are heated to produce the integrated structure of FIG. 813 The reinforced section 205A preferably has the same dimensions as the reinforced section 205 and the first, second and third lumens 219N, 221N, 223 preferably have the same dimensions as the aortic occlusion catheters described above.

Figure 13:
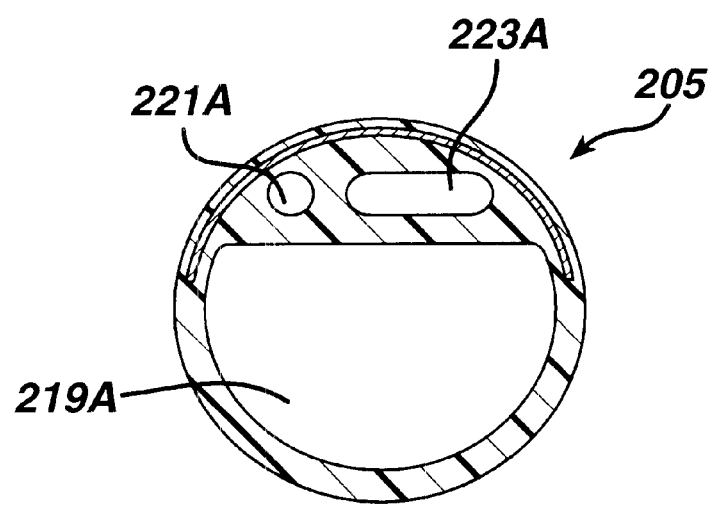
FIG. 13 is a cross-sectional view of FIG. 12 after fusing together the member and coated elongate member.
Figure 14:
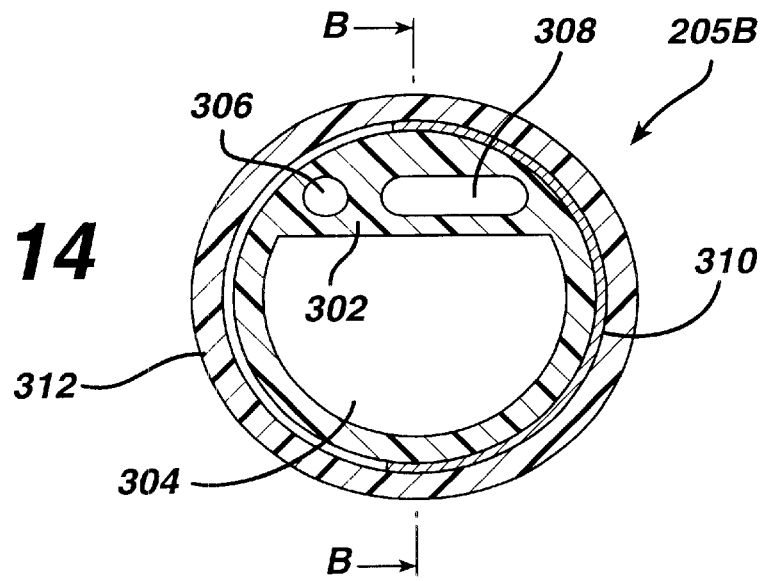
FIG. 14 is a cross-sectional view of yet another reinforced section for the aortic occlusion catheter.
Figure 15:
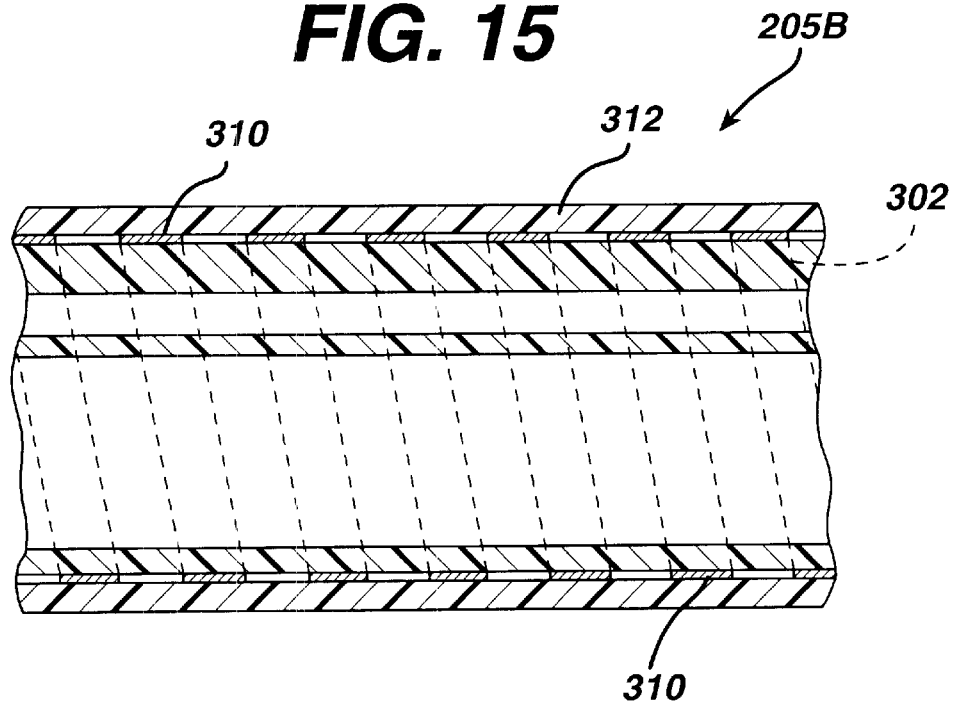
FIG. 15 is a longitudinal cross-sectional view of FIG. 14 around line B—B.

Referring to FIG. 14, yet another reinforced section 205B is shown. The reinforced section 205B includes an extrusion 302, which forms a single integrally foremost structure preferably having first, second and third lumens 304, 306, 308 An elongate member 310, which may be any of the elongate members described herein, is wrapped around the extrusion 302. A preferred elongate member 310 is a stainless steel ribbon having a width of 0.003 inch and a height of 0.012 inch. Referring to FIG. 15, the elongate member 310 is preferably wound so that adjacent portions are spaced apart between 0.010 and 0.020 inch. A tube 312, which is preferably made of polyurethane and preferably has a thickness of between 0.002 and 0.006 inch, is positioned over the elongate member 310. A shrink tube (not shown) is then positioned over the tube 312 and blockers are positioned in the lumens 304, 306, 308. The tube 312 and extrusion 302 are then heated so that they bond together and form an integral structure with the elongate member 310. The shrink tube, mandrel and blockers are removed and the resulting structure is essentially the same as the reinforced section 205 of FIG. 13. Although it is preferred to provide the tube 312, the elongate member 310 may also be dipped in a polymer solution to encase the elongate member 310 in polymer.

Figure 16:
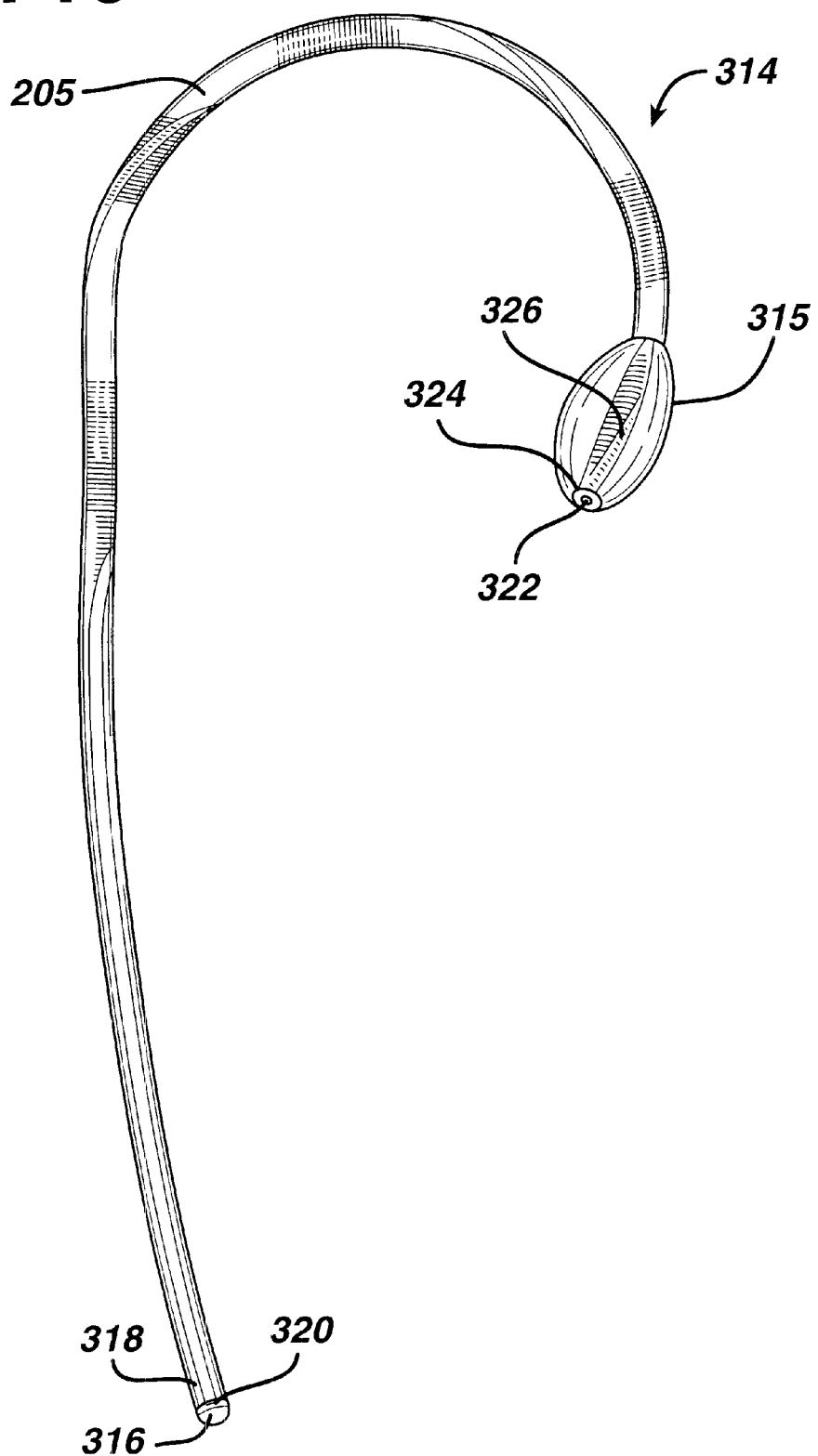
FIG. 16 shows an aortic occlusion catheter having one of the reinforced sections disclosed herein.

Referring to FIG. 16, the reinforced sections 205, 205A, 205B are useful for reinforcing an aortic occlusion catheter 314. The aortic occlusion catheter 314 may take any of the forms described herein and the entire discussion of aortic occlusion catheters is incorporated here including, for example, all preferred dimensions, shapes and methods of use. The aortic occlusion catheter 314 has an occluding member 315, which is preferably an inflatable balloon, at the distal end.

The reinforced section 205 is preferably formed so that first, second and third lumens 316, 318, 320 wind in a helical manner as shown in FIG. 16. By winding the reinforced section 250 in a helical manner the reinforced section 205 does not have any particular axis which is susceptible to kinking. It has been found that upon winding the coated elongate members around the mandrel and heating the elongate members, the resulting reinforced section twists when cooled so that the reinforced section naturally has the helical shape. Alternatively, the catheter may be twisted after forming or may be twisted during heating if pliable mandrels and blockers are used. Although it is preferred to wind the reinforced section 205 in a helical manner, the reinforced section 205 may also be formed without twisting. The first lumen 316 is used for infusion of cardioplegic fluid and an outlet 322 is provided distal to the occluding member 315 for infusing cardioplegic fluid to a patient's ascending aorta in the manner described above. The second lumen 318 also has an outlet 324 distal to the occluding member 315 which is preferably used for sensing a pressure in the patient's ascending aorta. The third lumen 320 is fluidly coupled to the occluding member 315 through an outlet 326 for inflating the occluding member 315. An advantage of using the reinforced section 205 is that the reinforcing coil does not extend around the inflation lumen 320 so that the reinforcing coil does not have to be penetrated when creating the outlet 326 in the inflation lumen 320. The reinforced section 205 extends around the shaped-end of the aortic occlusion catheter 314 which is particularly susceptible to kinking. The shaped-end of the aortic occlusion catheter 314 is preferably curved to facilitate placement of the occluding member 315 in the ascending aorta. The distal end is also preferably offset from a proximal portion in the manner described below in connection with FIGS. 17 and 18.

The occluding member 315 is preferably mounted to the reinforced section 250. The occluding member 315 preferably extends beyond the distal tip of the shaft when in the expanded shape (not shown) so that the occluding member acts as a bumper which prevents a distal end 328 from contacting the aorta or the aortic valve. The reinforced section 205 may extend throughout the aortic occlusion catheter 314 but preferably only extends around the portion which passes through the aortic arch. As such, the reinforced section 205 preferably extends 10 inches from a distal end 328 and more preferably 15 inches from the distal end 328.

Figure 17:
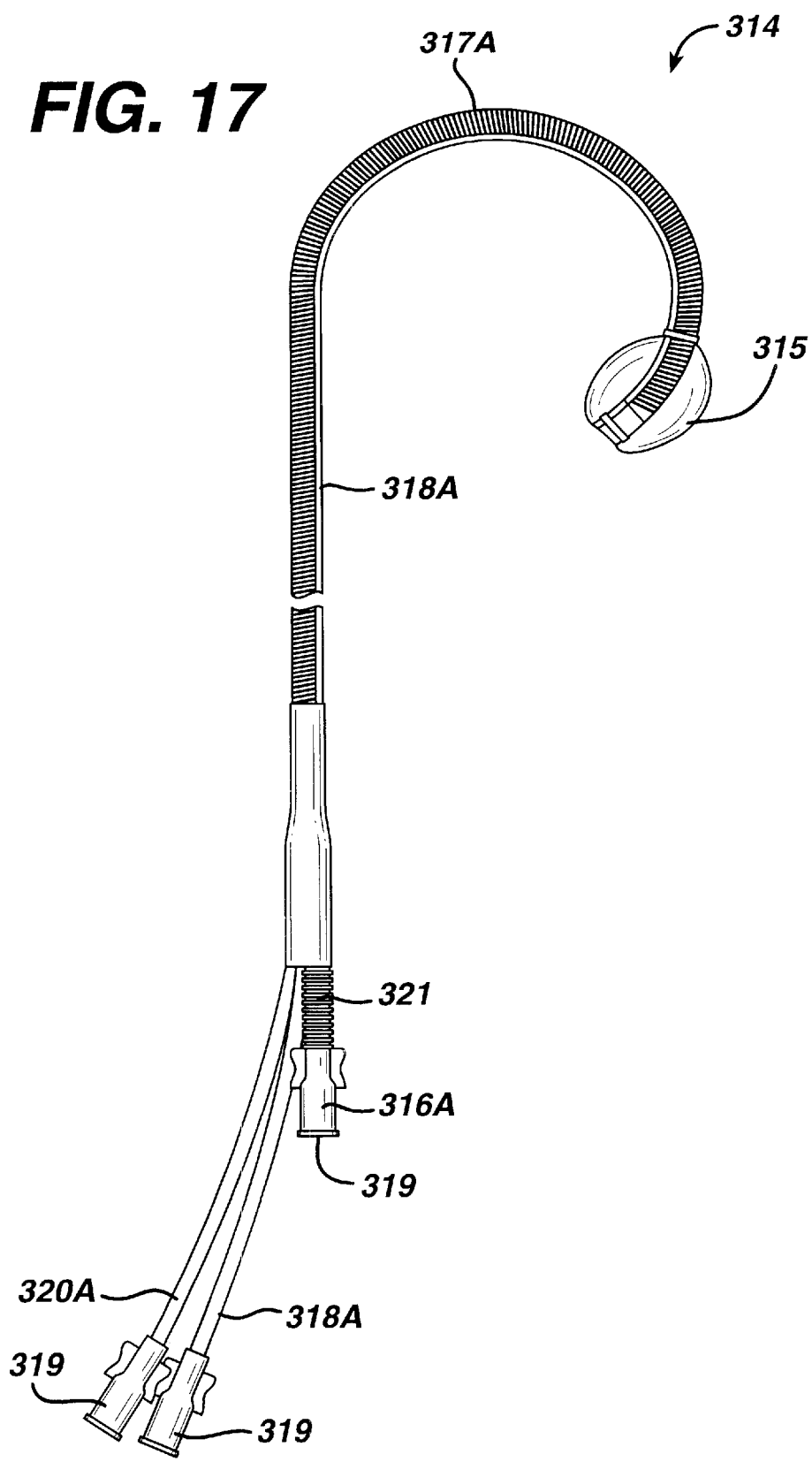
FIG. 17 is a side view of another aortic occlusion catheter.

Referring to FIG. 17, another reinforced aortic occlusion catheter 314A is shown. The aortic occlusion catheter 314A is used for the same purpose as the aortic occlusion catheter 314 and like reference numerals refer to like structures. The aortic occlusion catheter 314A has an occluding member 315, which is preferably an inflatable balloon, at a distal end. The aortic occlusion catheter 314A also has first, second and third lumens 316A, 318A, 320A which are used for the same purpose as the lumens 316, 318, 320 of the aortic occlusion catheter 314 described above. Each lumen has a connector 319 at a proximal end and the lumen 319 has a bellows 321 connection to increase flexibility and eliminate kinking at the proximal end.

Figure 18:
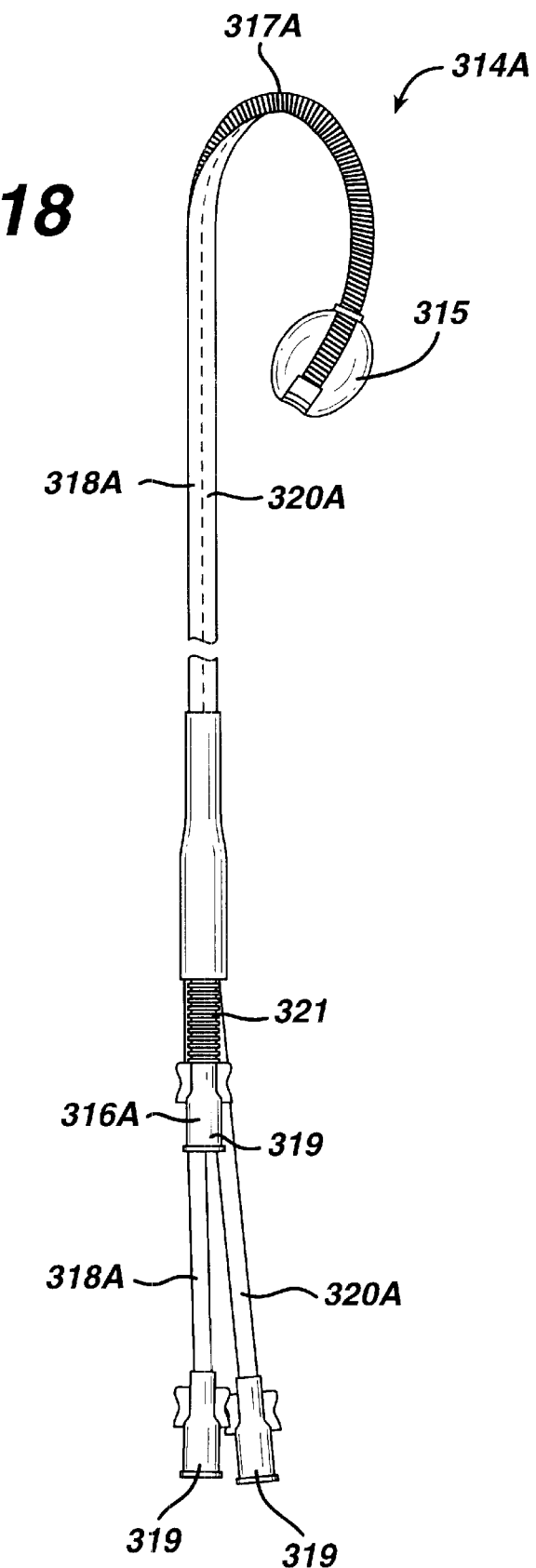
FIG. 18 is another side view of the aortic occlusion catheter of FIG. 17.

Referring to FIGS. 17 and 18, the lumens 316A, 318A, 320A do not wind in a helical manner like the lumens 316, 318, 320 of the aortic occlusion catheter 314 but, instead, run straight along the catheter 314. The lumens 318A, 320A, which are for balloon inflation and pressure monitoring, are preferably positioned on the radially inner portion of the catheter 314A in relation to a curved distal portion 317A. The curved distal portion 317A facilitates positioning the occluding member 315 in the ascending aorta. Referring to FIG. 18, the curved distal portion is also preferably offset somewhat. The resulting curved distal portion generally conforms to the aortic arch to facilitate placement of the occluding member 315 in the ascending aorta.

Figures 21, 22:
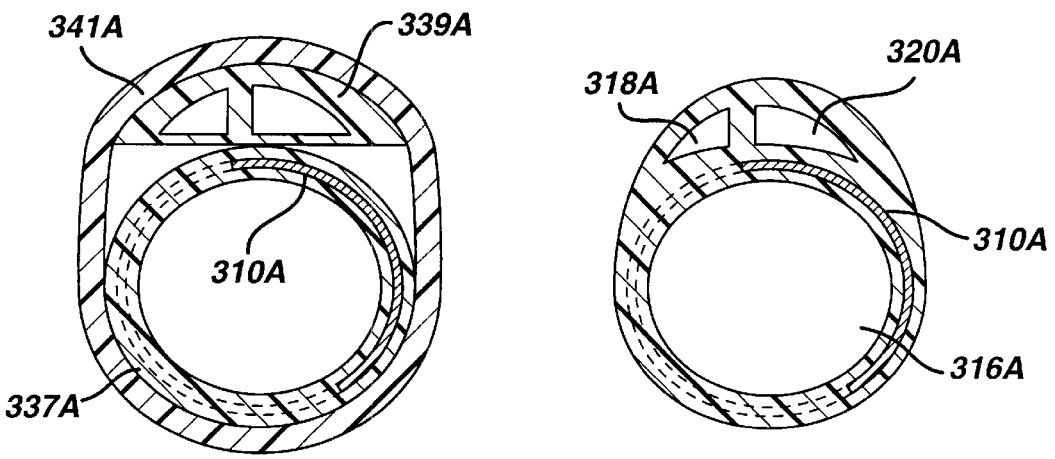
FIG. 21 is a cross-sectional view showing the manufacture of the aortic occlusion catheter of FIG. 17.
FIG. 22 is a cross-sectional view of the structure of FIG. 21 after heating.

Referring to FIG. 22, a cross-section of the catheter 314A is shown. The cross-sectional shape of the catheter 314A is somewhat egg-shaped but may, of course, also be substantially circular or any other suitable shape. An elongate element 310A which is described below, reinforces the catheter 314A. The elongate element 310A preferably extends throughout the length of the catheter 314A.

Figure 19:
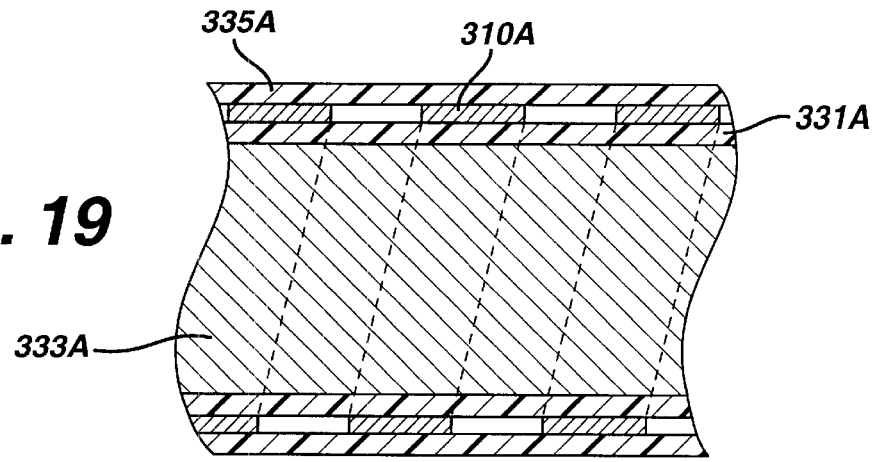
FIG. 19 is a longitudinal cross-sectional view showing the method of constructing the catheter of FIG. 17.
Figure 20:
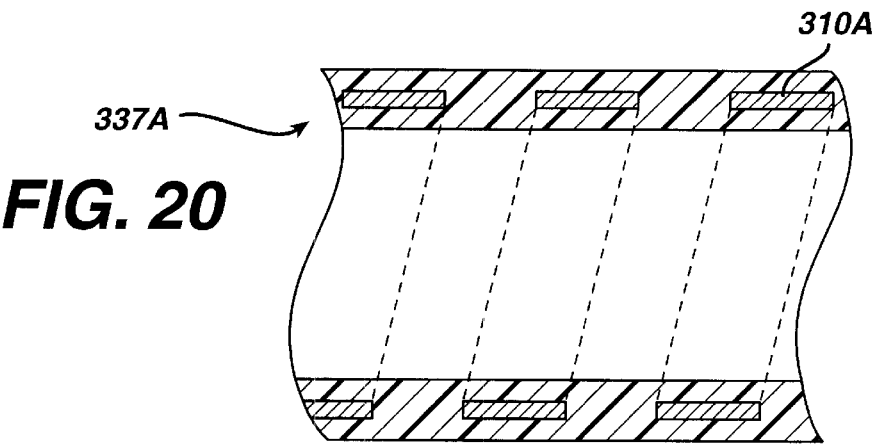
FIG. 20 is a longitudinal cross-sectional view showing the structure of FIG. 19 after heating.

Referring to FIGS. 19–21, a preferred method of forming the catheter 314A is shown. FIG. 19 shows a longitudinal cross-section of a tube 331A, preferably a urethane tube, mounted on a teflon-coated mandrel 333A with the reinforcing elongate element 310A wound around the tube 331A in a helical manner. The elongate element 310A is preferably a wire ribbon having a thickness of 0.003 inch and a width of 0.012 inch. The elongate element 310A is preferably wrapped around the tube 331A with a spacing of 0.010 inch. Another tube 335A is positioned over the elongate member 310A and a shrink tube (not shown) is positioned over the tube 335A. The entire structure is then heated to fuse the tubes together to form a reinforced tube 337A which is shown in longitudinal cross-section in FIG. 20. The resulting reinforced tube 337A preferably has an inner diameter of about 0.100 inch and a wall thickness of about 0.010 inch.

Referring to FIG. 21, a two-lumen member 339A is positioned against the reinforced tube 337A and a shrink tube 341A is positioned around the member 339A and reinforced tube 337A. The two-lumen member 339A has the lumen 320A, which is used for inflating the balloon, and the 318A lumen, which is used for pressure monitoring distal to the occluding member 315. The two-lumen member 339A is preferably an extrusion having a D-shaped outer surface in cross-section. The member 339A and tube 337A are then heated and the shrink tube 341A is removed to obtain the egg-shaped cross-sectional shape shown in FIG. 22. The cross-sectional shape is preferably about 0.145 inch tall and 0.125 inch wide. The inflation lumen 320A is then pierced to provide an inflation path to the occluding member 315 and the occluding member 315 is then mounted to the catheter 314A.

The methods and devices disclosed herein have been described in conjunction with catheters, however, it is understood that the methods and apparatus may also be used for constructing any other hollow tubes. While the above is a preferred description of the invention, various alternatives, modifications and equivalents may be used without departing from the scope of the invention. For example, the opposing sides of the coated elongate member 207 may have an S-shape, and the reinforced section 205 may have a varying wall thickness. Therefore, the above description should not be taken as limiting the scope of the invention which is defined by the claims.

What is claimed is:

1. A method of forming a catheter for occluding a patient's ascending aorta and delivering cardioplegic fluid to the patient's heart, comprising the steps of:

providing a single integrally formed structure having a first lumen and a second lumen, the first lumen having a cross-sectional size of 0.00754 to 0.01053 inch$^2$;

winding a helical reinforcing member around the single integrally formed structure, the helical reinforcing member having a thickness of between 0.006 and 0.012 and a height of between 0.002 and 0.004 inch;

positioning an outer wall around the helical reinforcing member, the outer wall having an outer diameter of 0.131 to 0.140 inch;

attaching an occluding member to the outer wall, the occluding member being movable from a collapsed condition to an expanded condition, the occluding member being configured to occlude a patient's ascending aorta when in the expanded condition.

2. The method of claim 1, wherein:

the second lumen has a cross-sectional size of 0.00095 to 0.0015 inch$^2$.

* * * * *